US010273487B2

(12) United States Patent
Seyfang et al.

(10) Patent No.: US 10,273,487 B2
(45) Date of Patent: Apr. 30, 2019

(54) TRANSFECTION VECTOR FOR PATHOGENIC AMOEBAE AND USES THEREOF

(71) Applicants: Andreas Seyfang, Tampa, FL (US); Christopher L. Massengill, Odessa, FL (US); Sara R. Sievers, San Carlos, CA (US)

(72) Inventors: Andreas Seyfang, Tampa, FL (US); Christopher L. Massengill, Odessa, FL (US); Sara R. Sievers, San Carlos, CA (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/894,746

(22) Filed: Feb. 12, 2018

(65) Prior Publication Data

US 2018/0245086 A1 Aug. 30, 2018

Related U.S. Application Data

(60) Provisional application No. 62/457,586, filed on Feb. 10, 2017.

(51) Int. Cl.

*C12N 15/65* (2006.01)
*C12N 15/79* (2006.01)
*C12N 15/87* (2006.01)
*C12N 1/10* (2006.01)
*C12N 13/00* (2006.01)
*A61K 39/00* (2006.01)
*A61K 39/002* (2006.01)

(52) U.S. Cl.

CPC ............ *C12N 15/65* (2013.01); *A61K 39/002* (2013.01); *C12N 1/10* (2013.01); *C12N 13/00* (2013.01); *C12N 15/79* (2013.01); *C12N 15/87* (2013.01); *A61K 2039/51* (2013.01); *A61K 2039/522* (2013.01); *C12N 2830/50* (2013.01)

(58) Field of Classification Search

CPC .......... C12N 15/65; C12N 15/79; C12N 1/10; C12N 13/00; C12N 15/87; C12N 2830/50; A61K 39/002; A61K 2039/522; A61K 2039/51

See application file for complete search history.

(56) References Cited

PUBLICATIONS

Burland et al., Gene 132(2):207-212, 1993.*
Burland et al., Current Genetics 21:393-398, 1992.*
Gritz et al., Gen Bank accession No. K01193, 1994.*
Hotez et al., Vaccine 24:5787-5799, 2006.*
"Development of a Naegleria fowleri Transfection Vector as Novel Genetic Tool in Pathogenic Ameba," poster presented Feb. 19, 2016 at USF Research Day 2016.
Boshart et al., "A very strong enhancer is located upstream of an immediate early gene of human cytomegalovirus," Cell, 1985, 41(2):521-30.
Chalfie et al., "Green fluorescent protein as a marker for gene expression," Science, 1994, 263(5148):802-805.
Cormack et al., "FACS-optimized mutants of the green fluorescent protein (GFP)," Gene, 1996, 173:33-38.
Dijkema et al., "Cloning and expression of the chromosomal immune interferon gene of the rat," EMBO J., 1985, 4(3):761-767.
Genbank Accession No. AB041904 (2003).
Genbank Accession No. AB085641 (2002).
Genbank Accession No. AB195239 (2007).
Genbank Accession No. AF058694 (2009).
Genbank Accession No. AF058695 (1998).
Genbank Accession No. AF168419 (2001).
Genbank Accession No. AF168420 (2001).
Genbank Accession No. AF183395 (2000).
Genbank Accession No. AF272711 (2000).
Genbank Accession No. AF302837 (2001).
Genbank Accession No. AF420593 (2002).
Genbank Accession No. AF435427 (2006).
Genbank Accession No. AF435428 (2006).
Genbank Accession No. AF435429 (2006).
Genbank Accession No. AF435430 (2006).
Genbank Accession No. AF435431 (2006).
Genbank Accession No. AF435432 (2006).
Genbank Accession No. AF435433 (2006).
Genbank Accession No. AF435434 (2016).
Genbank Accession No. AF506025 (2002).
Genbank Accession No. AF506026 (2002).
Genbank Accession No. AF506027 (2002).
Genbank Accession No. AF545828 (2004).
Genbank Accession No. AX250563 (2001).
Genbank Accession No. AX250564 (2001).
Genbank Accession No. AX250565 (2001).
Genbank Accession No. AX250566 (2001).
Genbank Accession No. AX250567 (2001).
Genbank Accession No. AX250568 (2001).
Genbank Accession No. AX250569 (2001).
Genbank Accession No. AX250570 (2001).
Genbank Accession No. AX250571 (2001).
Genbank Accession No. AY013821 (2002).
(Continued)

*Primary Examiner* — Delia M Ramirez
(74) *Attorney, Agent, or Firm* — Michael Best & Friedrich LLP

(57) ABSTRACT

Disclosed herein are expression vectors suitable for transfection in amoebas. The vectors may include a promoter from a protein-encoding gene from an amoeba, a selection marker, and a polynucleotide sequence encoding a polypeptide of interest, operably linked to the promoter. The promoter may be from the ACT1 gene from *Naegleria fowleri*.

12 Claims, 6 Drawing Sheets

Specification includes a Sequence Listing.

(56) References Cited

PUBLICATIONS

Genbank Accession No. AY013824 (2006).
Genbank Accession No. AY013825 (2006).
Genbank Accession No. AY013826 (2006).
Genbank Accession No. AY013827 (2006).
Genbank Accession No. AY533296 (2004).
Genbank Accession No. AY678264 (2004).
Genbank Accession No. AY678265 (2004).
Genbank Accession No. AY678266 (2004).
Genbank Accession No. AY678267 (2004).
Genbank Accession No. AY678268 (2004).
Genbank Accession No. AY678269 (2004).
Genbank Accession No. AY678270 (2004).
Genbank Accession No. AY678271 (2004).
Genbank Accession No. AY679106 (2005).
Genbank Accession No. AY679107 (2004).
Genbank Accession No. AY679108 (2005).
Genbank Accession No. AY786536 (2004).
Genbank Accession No. AY786537 (2004).
Genbank Accession No. BAC20344 (2002).
Genbank Accession No. BD136947 (2002).
Genbank Accession No. BD136948 (2002).
Genbank Accession No. BD136949 (2002).
Genbank Accession No. BD440518 (2005).
Genbank Accession No. BD440519 (2005).
Genbank Accession No. DD420089 (2007).
Genbank Accession No. DD420090 (2007).
Genbank Accession No. DD420091 (2007).
Genbank Accession No. DD431502 (2007).
Genbank Accession No. DD431503 (2007).
Genbank Accession No. DD431504 (2007).
Genbank Accession No. DQ092360 (2006).
Genbank Accession No. DQ092361 (2006).
Genbank Accession No. DQ092362 (2006).
Genbank Accession No. DQ092363 (2006).
Genbank Accession No. DQ092364 (2006).
Genbank Accession No. DQ092365 (2006).
Genbank Accession No. DQ301560 (2006).
Genbank Accession No. DQ525024 (2006).
Genbank Accession No. DQ525025 (2006).
Genbank Accession No. EF064258 (2006).
Genbank Accession No. EF064259 (2006).
Genbank Accession No. L29345 (1994).
Genbank Accession No. M62653 (1993).
Genbank Accession No. M62654 (1993).
Genbank Accession No. U50963 (1996).
Genbank Accession No. U73901 (2018).
Genbank Accession No. X83959 (2016).
Genbank Accession No. X83960 (2016).
Genbank Accession No. X96418 (2000).
Gorman et al., "The Rous sarcoma virus long terminal repeat is a strong promoter when introduced into a variety of eukaryotic cells by DNA-mediated transfection," Proc Natl Acad Sci U S A., 1982, 79(22):6777-6781.
Gorman, C. (1985) In DNA Cloning: A Practical Approach, vol. II, Ed. Glover, D. M. (IRL Press, Oxford, UK) pp. 143-190.
Haas et al., "Codon usage limitation in the expression of HIV-1 envelope glycoprotein," Curr. Biol., 1996, 6(3):315-324.
Hanks et al., "Protein kinases 6. The eukaryotic protein kinase superfamily: kinase (catalytic) domain structure and classification," FASEB J., 1995, 9(8):576-595.
Heagerty et al., "Time-dependent ROC curves for censored survival data and a diagnostic marker," Biometrics, 2000, 56(2):337-44.
Inouye et al., "Aequorea green fluorescent protein. Expression of the gene and fluorescence characteristics of the recombinant protein," FEBS Letters, 1994, 341(2-3):277-280.
Kim et al., "Use of the human elongation factor 1 alpha promoter as a versatile and efficient expression system," Gene, 1990, 91(2):217-23.
Kozak, "An analysis of 5'-noncoding sequences from 699 vertebrate messenger RNAs," Nucleic Acids Res, 1987, 15(20):8125-8148.
Kyte et al., "A simple method for displaying the hydropathic character of a protein," J. Mol. Biol., 1982, 157(1):105-132.
Maniatis et al., "Regulation of inducible and tissue-specific gene expression," Science, 1987, 236(4806):1237-45.
Mayer et al., "Signalling through SH2 and SH3 domains," Trends Cell. Biol., 1993, 3(1):8-13.
Mizushima et al., "pEF-BOS, a powerful mammalian expression vector," Nucleic Acids Res, 1990, 18(17):5322.
Prasher et al., "Primary structure of the Aequorea victoria green-fluorescent protein," Gene, 1992, 111(2):229-233.
Sadowski et al., "A noncatalytic domain conserved among cytoplasmic protein-tyrosine kinases modifies the kinase function and transforming activity of Fujinami sarcoma virus P130gag-fps," Mol. Cell. Bio., 1986, 6(12):4396-4408.
Sambrook et al., Molecular Cloning: A Laboratory Manual, 2nd ed., Cold Spring Harbor Laboratory Press, New York (1989) pp. 16.7-16.8.
Uetsuki et al., "Isolation and characterization of the human chromosomal gene for polypeptide chain elongation factor-1 alpha," J. Biol. Chem., 1989, 264(10):5791-8.
Voss et al., "The role of enhancers in the regulation of cell-type-specific transcriptional control," Trends Biochem. Sci., 1986, 11(7):287-289.

* cited by examiner

Construction of *pNfEGFP-Hyg* Transfection Vector

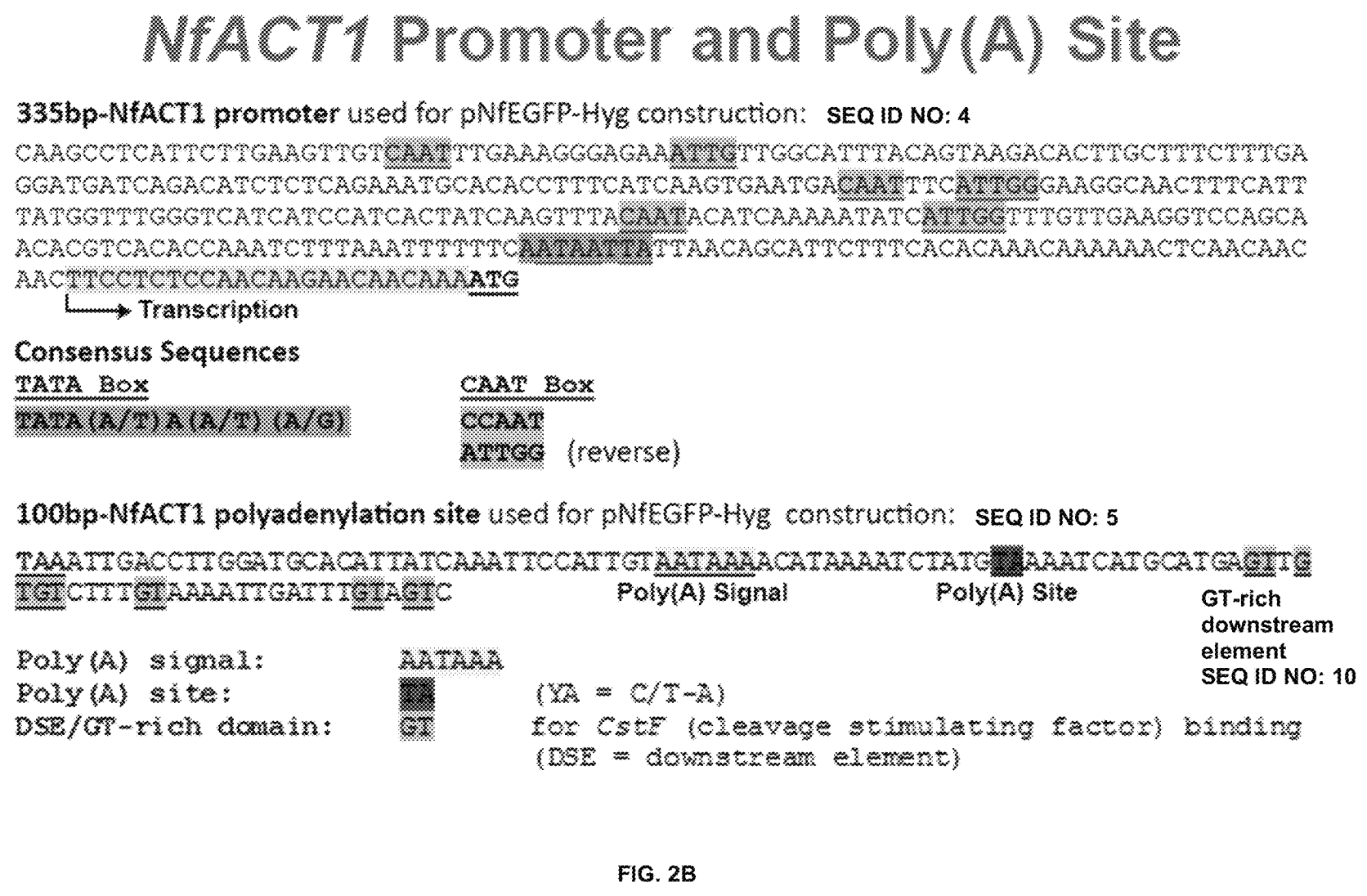

*NfACT1* Promoter and Poly(A) Site

335bp-NfACT1 promoter used for pNfEGFP-Hyg construction: SEQ ID NO: 4

```
CAAGCCTCATTCTTGAAGTTGTCAATTTGAAAGGGAGAAATTGTTGGCATTTACAGTAAGACACTTGCTTTCTTTGA
GGATGATCAGACATCTCTCAGAAATGCACACCTTTCATCAAGTGAATGACAATTTCATTGGGAAGGCAACTTTCATT
TATGGTTTGGGTCATCATCCATCACTATCAAGTTTACAATACATCAAAAATATCATTGGTTTGTTGAAGGTCCAGCA
ACACGTCACACCAAATCTTTAAATTTTTTCAATAATTATTAACAGCATTCTTTCACACAAACAAAAAACTCAACAAC
AACTTCCTCTCCAACAAGAACAACAAAATG
```

└──→ Transcription

Consensus Sequences

| TATA Box | CAAT Box |
|---|---|
| TATA(A/T)A(A/T)(A/G) | CCAAT |
| | ATTGG (reverse) |

100bp-NfACT1 polyadenylation site used for pNfEGFP-Hyg construction: SEQ ID NO: 5

```
TAAATTGACCTTGGATGCACATTATCAAATTCCATTGTAATAAAACATAAAATCTATG[illegible]AAATCATGCATGAGTTG
TGTCTTTGTAAAATTGATTTGTAGTC
```

Poly(A) Signal — Poly(A) Site — GT-rich downstream element SEQ ID NO: 10

| | | |
|---|---|---|
| Poly(A) signal: | AATAAA | |
| Poly(A) site: | [illegible] | (YA = C/T-A) |
| DSE/GT-rich domain: | GT | for *CstF* (cleavage stimulating factor) binding (DSE = downstream element) |

FIG. 2B

TRANSFECTION VECTOR FOR PATHOGENIC AMOEBAE AND USES THEREOF

CROSS-REFERENCE TO RELATED APPLICATION(S)

This application claims priority to U.S. Provisional Patent Application No. 62/457,586, filed on Feb. 10, 2017, which is incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 21,237 Byte ASCII (Text) file named "17A009PRC-210112-9028-US02_ST25.txt", created on May 7, 2018.

FIELD

This disclosure relates to vectors suitable for transfecting pathogenic amoeba and methods of using the same.

INTRODUCTION

Free-living pathogenic amoeba can cause serious and often fatal diseases. For example, *Naegleria fowleri* from fresh water lakes or pools can cause primary amoebic meningoencephalitis (PAM) with a 98-99% fatality rate. *Acanthamoeba* spp. or *Balamuthia mandrillaris* from soil or contaminated fresh water can cause fatal granulomatous amoebic encephalitis (GAE). *Acanthamoeba* spp can also cause amoebic keratitis and is a particular threat for people wearing contact lenses. There is currently no effective drug treatment for PAM and other diseases caused by amoeba. The lack of efficient drugs is compounded by the difficulty of drug delivery across the blood-brain barrier.

SUMMARY

In an aspect, the disclosure relates to an expression vector. The expression vector may include a promoter from a protein-encoding gene from an amoeba; a selection marker selected from hygromycin resistance gene, puromycin resistance gene, nourseothricin resistance gene, and bleomycin resistance gene; and a nucleic acid sequence encoding a polypeptide of interest, operably linked to the promoter. In some embodiments, the amoeba is *N. fowleri*. In some embodiments, the promoter is from the ACT1 gene from *N. fowleri*. In some embodiments, the promoter comprises a polynucleotide sequence of SEQ ID NO: 4. In some embodiments, the vector further comprises a poly(A) site, operably linked to the promoter. In some embodiments, the poly(A) site comprises a polynucleotide sequence of SEQ ID NO: 5. In some embodiments, the selection marker is positioned downstream of the promoter and upstream of the poly(A) site. In some embodiments, the selection marker comprises the hygromycin resistance gene. In some embodiments, the hygromycin resistance gene comprises a polynucleotide sequence of SEQ ID NO: 6. In some embodiments, the vector does not include a cytomegalovirus (CMV) promoter. In some embodiments, the vector further comprises a multiple cloning site (MCS), wherein the promoter is upstream of the MCS. In some embodiments, the promoter, poly(A) site, and selection marker are upstream of the MCS. In some embodiments, the MCS comprises a polynucleotide sequence of SEQ ID NO: 3. In some embodiments, the vector further comprises a polynucleotide encoding a fluorescent protein. In some embodiments, the polynucleotide encoding a fluorescent protein is operably linked to the promoter and to the polypeptide of interest. In some embodiments, the vector comprises a polynucleotide sequence of SEQ ID NO: 7.

In a further aspect, the disclosure relates to an amoeba transformed with the vector as detailed herein. In some embodiments, the amoeba has reduced virulence compared to a control amoeba. In some embodiments, the control comprises an untransformed amoeba or an amoeba transformed with a different vector.

Another aspect of the disclosure provides a vaccine comprising the amoeba transformed with the vector as detailed herein.

Another aspect of the disclosure provides a method of expressing a foreign protein in an amoeba. The method may include transforming an amoeba with the vector as detailed herein, wherein the polypeptide of interest comprises the foreign protein; isolating the transformed amoeba; and expressing the foreign protein in the amoeba.

Another aspect of the disclosure provides a method of manipulating an amoeba genome. The method may include transforming the amoeba with the vector as detailed herein; isolating the transformed amoeba; and expressing the polypeptide of interest in the amoeba.

In some embodiments, the transforming is performed by electroporation. In some embodiments, the isolating comprises culturing the amoeba in the presence of hygromycin, puromycin, nourseothricin, or bleomycin, or a combination thereof.

The disclosure provides for other aspects and embodiments that will be apparent in light of the following detailed description and accompanying figures.

BRIEF DESCRIPTION OF THE DRAWINGS

FIG. 2B is a schematic diagram of the NfACT1 promoter and poly(a) site of the pNfEGFP-Hyg vector.

DETAILED DESCRIPTION

Figure 1:
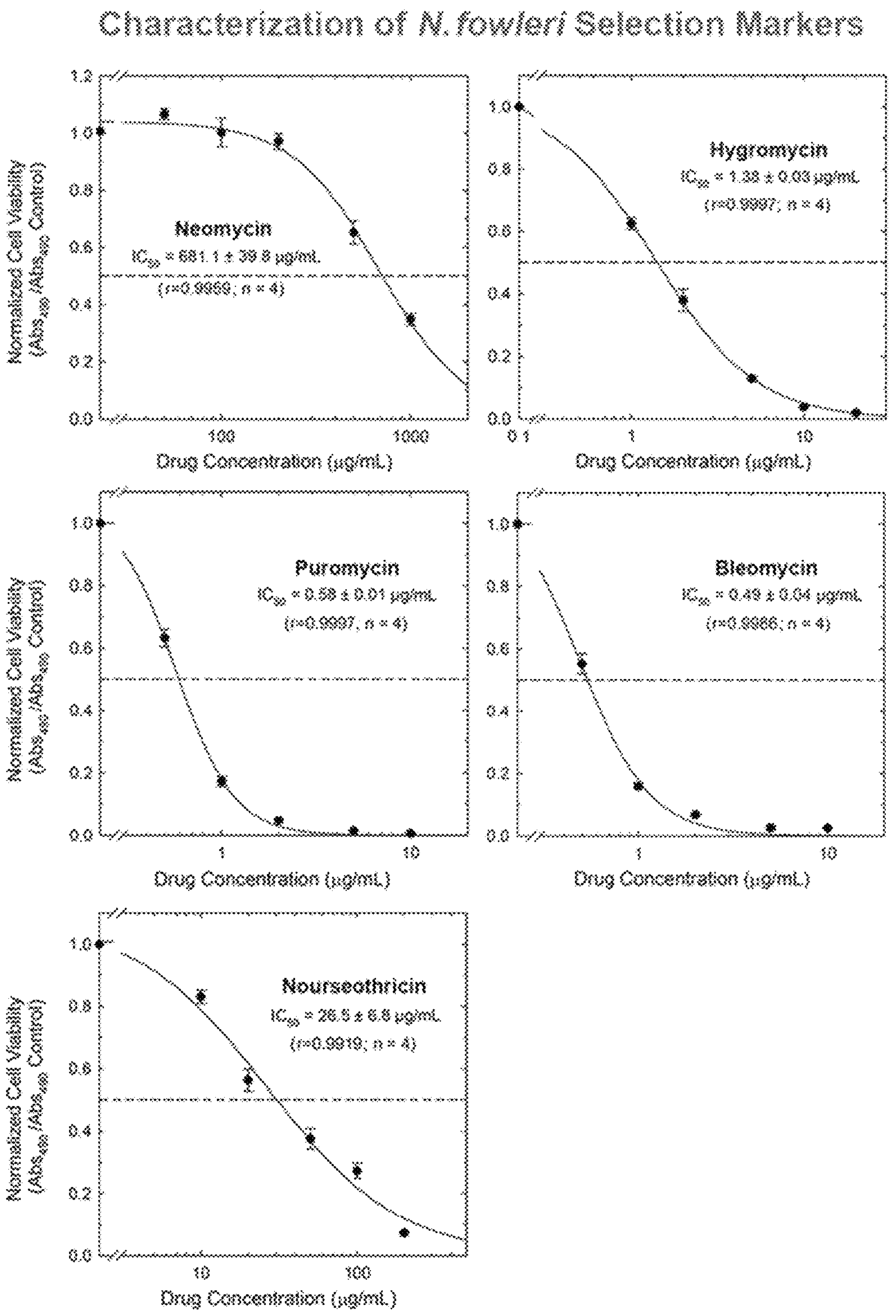
FIG. 1 are graphs of cell viability versus drug concentration for various selection markers.

Described herein are expression vectors with selection markers and promoters that may be used to successfully transfect amoebas. Preliminary studies revealed that the amoeba *Naegleria fowleri* has natural resistance to the common selection marker neomycin, rendering neomycin ineffective as a selection marker for amoebas. Conventional mammalian transfection vectors include mammalian-specific promoters, such as the CMV promoter, that are not suitable for amoebic transfection. As detailed herein, selection markers and promoters suitable for use in the amoeba *N. fowleri* were discovered. The suitable selection markers and promoters may be used in expression vectors for transfecting amoeba such as *N. fowleri* and expressing proteins of interest. Multiple selectable markers may facilitate multiple rounds of transfection with different genes in reverse genetics approaches or for selection of double-knockouts in forward genetics screens. The expression vectors detailed herein provide an important tool for molecular and cellular analysis of amoebic virulence factors, as well as for reverse genetics approaches to examine potential drug targets within these pathogenic amoebae. The ability to introduce and express genes in amebae may facilitate both genetic analysis and modification of the virulence of this organism, which remains a serious threat to world health, and facilitate basic research towards the control of this parasite.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administration" or "administering," as used herein, refers to providing, contacting, and/or delivery of a compound, vector, or agent, etc., by any appropriate route to achieve the desired effect. These compounds or agents may be administered to a subject in numerous ways including, but not limited to, orally, ocularly, nasally, intravenously, topically, as aerosols, suppository, etc. and may be used in combination.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The term "antagonist" or "inhibitor" refers to a substance that blocks (e.g., reduces or prevents) a biological activity. An inhibitor may inhibit an activity directly or indirectly.

As used herein, the term "agonist" refers to a substance that triggers (e.g., initiates or promotes), partially or fully enhances, stimulates, or activates one or more biological activities. An agonist may mimic the action of a naturally occurring substance. Whereas an agonist causes an action, an antagonist blocks the action of the agonist.

"Antimicrobial" or "antibiotic" refers to a substance or method that is able to kill or inhibit the growth of microorganisms. To "kill or inhibit the growth of" includes limiting the presence of at least one microorganism. To "kill or inhibit the growth of" also includes inactivation or prevention of the replication of or reducing the number of a microorganism. Antibiotics include, for example, penicillin such as penicillin G, penicillin V, penicillin G benzathine, ampicillin, anoxacillin, nafcillin, carbenicilllin, dicloxacillin, bacampicillin, piperacillin, ticaricillin, mezlocillin and the like; cephalosporins such as cefazolin, cefadroxil, cephalexin, cefaclor, cefoxitin, cefonicid, ceftizoxime, cefprozil, ceftazidine, cefixime, cefpodoxime proxitel and the like; aminoglycosides such as amikacin, gentamicin, tobramycin, netilmicin, hygromycin, streptomycin, nourseothricin and the like; macrolides such as erythromycin and the like; monobactams such as aztreonam and the like; rifamycin and derivatives such as rifampin, rifamide, rifaximin and the like; chloramphenicol, clindamycin, lincomycin, imipenem, vancomycin; tetracyclines such as chloretetracycline, tetracycline, minocycline, doxycycline and the like; fusidic acid, novobiocin and the like; fosfomycin, fusidate sodium, neomycin, bacitracin, polymyxin, capreomycin, colistimethate, colistin, sulfamethoxazole, trimethoprim, puromycin, bleomycin, and gramicidin, and combinations thereof.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, diseased after treatment, or healthy after treatment, or a combination thereof. The term "normal subject" as used herein means a healthy subject, i.e. a subject having no clinical signs or symptoms of disease. The normal subject is clinically evaluated for otherwise undetected signs or symptoms of disease, which evaluation may include routine physical examination and/or laboratory testing. In some embodiments, the control is a healthy control. In some embodiments, the control comprises neurodegenerative disease.

As used herein, the term "cloning" refers to the process of ligating a polynucleotide into a vector and transferring it into an appropriate host cell for duplication during propagation of the host.

The term "effective amount," as used herein, refers to a dosage of the compounds or compositions effective for eliciting a desired effect. This term as used herein may also refer to an amount effective at bringing about a desired in vivo effect in a subject, such as in an animal, preferably, a human, such as treatment of a disease.

The term "host cell" is a cell that is susceptible to transformation, transfection, transduction, conjugation, and the like with a polynucleotide construct or expression vector. Host cells can be derived from plants, bacteria, yeast, fungi, insects, animals, protozoans, etc. In some embodiments, the host cell includes amoebas such as *N. fowleri.*

"Microorganism" refers to a unicellular or multi-cellular microscopic or macroscopic life form. Microorganisms include, for example, amoebas, bacteria, protobacteria, phytoplankton, fungi, viruses, algae, molds, oomycetes, parasites, nematodes, and protozoans, or any combination thereof. Microorganisms may also be referred to as microbes.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

Polynucleotides are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a polynucleotide sequence, even if internal to a larger oligonucleotide, also may be said to have 5' and 3' ends. In either a linear or circular polynucleotide, discrete elements are referred to as being "upstream" or 5' of the "downstream" or 3' elements. This terminology reflects the fact that transcription proceeds in a 5' to 3' fashion along the polynucleotide strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "gene" means the polynucleotide sequence comprising the coding region of a gene, e.g., a structural gene, and the including sequences located adjacent to the coding region on both the 5' and 3' ends for a distance of about 1 kb on either end such that the gene corresponds to the length of the full-length mRNA. The sequences which are located 5' or upstream of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA, for example, heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, an oligonucleotide or polynucleotide "having a nucleotide sequence encoding a gene" means a polynucleotide sequence comprising the coding region of a gene, or in other words, the nucleic acid sequence which encodes a gene product. The coding region may be present in either a cDNA, genomic DNA, or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the vector may contain endogenous enhancers/promoters, splice junctions, intervening sequences, polyadenylation signals, etc., or a combination of both endogenous and exogenous control elements.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide.

"Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units.

"Recombinant" when used with reference, e.g., to a cell, or polynucleotide, protein, or vector, indicates that the cell, nucleic acid, protein, or vector, has been modified by the introduction of a heterologous nucleic acid or protein or the alteration of a native polynucleotide or protein, or that the cell is derived from a cell so modified. Thus, for example, recombinant cells express genes that are not found within the native (non-recombinant) form of the cell or express native genes that are otherwise abnormally expressed, under expressed, or not expressed at all. For example, the term "recombinant DNA molecule" as used herein refers to a DNA molecule which is comprised of segments of DNA joined together by means of molecular biological techniques. The term "recombinant protein" or "recombinant polypeptide" as used herein refers to a protein molecule which is expressed from a recombinant DNA molecule or recombinant polynucleotide.

The term "native protein" as used herein to indicate that a protein does not contain amino acid residues encoded by vector sequences; the native protein contains only those amino acids found in the protein as it occurs in nature. A native protein may be produced by recombinant means or may be isolated from a naturally occurring source.

An "open reading frame" includes at least 3 consecutive codons which are not stop codons. The term "codon" as used herein refers to any group of three consecutive nucleotide bases in a given messenger RNA molecule, or coding strand of DNA or polynucleotide that specifies a particular amino acid, a starting signal, or a stopping signal for translation. The term codon also refers to base triplets in a DNA strand.

The terms "in operable combination," "in operable order," and "operably linked" as used herein refer to the linkage of polynucleotide sequences in such a manner that a polynucleotide molecule capable of directing the transcription of a given gene and/or the synthesis of a desired protein molecule is produced. The term also refers to the linkage of amino acid sequences in such a manner so that a functional protein is produced.

As used herein, the term "restriction endonuclease" or "restriction enzyme" refers to a member or members of a classification of catalytic molecules that bind a cognate sequence of a polynucleotide and cleave the polynucleotide at a precise location within that sequence. Restriction endonuclease may be bacterial enzymes. Restriction endonuclease may cut double-stranded DNA at or near a specific nucleotide sequence.

As used herein, "recognition site" or "restriction site" refers to a sequence of specific bases or nucleotides that is recognized by a restriction enzyme if the sequence is present in double-stranded DNA; or, if the sequence is present in single-stranded RNA, the sequence of specific bases or nucleotides that would be recognized by a restriction enzyme if the RNA was reverse transcribed into cDNA and the cDNA employed as a template with a DNA polymerase to generate a double-stranded DNA; or, if the sequence is present in single-stranded DNA, the sequence of specific bases or nucleotides that would be recognized by a restriction enzyme if the single-stranded DNA was employed as a template with a DNA polymerase to generate a double-stranded DNA; or, if the sequence is present in double-stranded RNA, the sequence of specific bases or nucleotides that would be recognized by a restriction enzyme if either strand of RNA was reverse transcribed into cDNA and the cDNA employed as a template with a DNA polymerase to generate a double-stranded DNA. The term "unique restriction enzyme site" or "unique recognition site" indicates that the recognition sequence for a given restriction enzyme appears once within a polynucleotide.

As used herein, the term "regulatory element" refers to a genetic element which controls some aspect of the expression of polynucleotide sequences. For example, a promoter is a regulatory element that facilitates the initiation of transcription of an operably linked coding region. Other regulatory elements may include splicing signals, polyadenylation signals, termination signals, and the like. Transcriptional control signals in eukaryotes include "promoter" and "enhancer" elements. Promoters and enhancers include short arrays of polynucleotide sequences that interact specifically with cellular proteins involved in transcription (Maniatis et al., Science, 236: 1237 (1987), incorporated herein by reference). Conventional promoter and enhancer elements have been isolated from a variety of eukaryotic sources such as, for example, genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss et al., Trends Biochem. Sci., 11:287 (1986) and Maniatis et al., supra (1987)). For example, the SV40 early gene enhancer is very active in a wide variety of cell types from many mammalian species and has been widely used for the expression of proteins in mammalian cells (Dijkema et al. EMBO J. 1985, 4, 761). Two other examples of promoter/enhancer elements active in a broad range of mammalian cell types are those from the human elongation factor 10 gene (Uetsuki et al. J. Biol. Chem. 1989, 264, 5791; Kim et al. Gene, 1990, 91, 217; Mizushima et al. Nuc. Acids. Res. 1990, 18, 5322) and the long terminal repeats of the Rous sarcoma virus (Gorman et al. Proc. Natl. Acad. Sci. USA 1982, 79, 6777) and the human cytomegalovirus (Boshart et al. Cell 1985, 41, 521).

As used herein, the term "promoter/enhancer" denotes a segment of a polynucleotide that contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

"Replication origins" are unique polynucleotide segments that contain multiple short repeated sequences that are recognized by multimeric origin-binding proteins and which play a key role in assembling DNA replication enzymes at the origin site.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York (1989) pp. 16.7-16.8). An example of a splice donor and acceptor site is the splice junction from the 16S RNA of SV40.

As used herein, the term "purified" or "to purify" or "isolate" refers to the removal of contaminants from a sample.

As used herein the term "portion" when in reference to a protein or polynucleotide (as in "a portion of a given protein") refers to fragments of that protein or polynucleotide. The protein fragments may range in size from two or more amino acid residues to the entire amino acid sequence minus one amino acid. Polynucleotide fragments may range in size from two or more nucleotides to the entire polynucleotide sequence minus one nucleotide.

As used herein, the term "fusion protein" refers to a chimeric protein containing the protein of interest joined to a different peptide or protein fragment. The fusion partner may, for example, enhance the solubility of a linked protein of interest, allow identification and/or purification of the recombinant fusion protein, may provide an epitope tag or affinity domain to allow identification and/or purification of the recombinant fusion protein, e.g., from a host cell which expresses the fusion or a culture supernatant of that cell, or both, or may have another property or activity, e.g., two functional enzymes can be fused to produce a single protein with multiple enzymatic activities. If desired, the fusion protein may be removed from the protein of interest by a variety of enzymatic or chemical means known to the art. Thus, examples of fusion protein producing sequences useful in the vectors of the invention include epitope tag encoding sequences, affinity domain encoding sequences, or other functional protein encoding sequences, and the like. The use of the term "functional protein encoding sequence," as used herein, indicates that the fusion protein producing element of a vector encodes a protein or peptide having a particular activity, such as an enzymatic activity, e.g., luciferase or dehalogenase, a binding activity, and the like, e.g., thioredoxin. For example, a functional protein encoding sequence may encode a kinase catalytic domain (Hanks and Hunter, FASEB J. 1995, 9, 576-595), producing a fusion protein that can enzymatically add phosphate moieties to particular amino acids, or may encode a Src Homology 2 (SH2) domain (Sadowski et al. Mol. Cell. Bio. 1986, 6, 4396; Mayer and Baltimore, Trends Cell. Biol. 1993, 3, 8), producing a fusion protein that specifically binds to phosphorylated tyrosines.

The term "specificity" as used herein refers to the number of true negatives divided by the number of true negatives plus the number of false positives, where specificity ("spec") may be within the range of 0<spec<1. Hence, a method that has both sensitivity and specificity equaling one, or 100%, is preferred.

"Sample" or "test sample" as used herein can mean any sample in which the presence and/or level of an activity, a biomarker, target, agent, vector, or molecule, etc., is to be detected or determined. Samples may include liquids, solutions, emulsions, mixtures, or suspensions. Samples may include a medical sample. Samples may include any biological fluid or tissue, such as blood, whole blood, fractions of blood such as plasma and serum, peripheral blood mononuclear cells (PBMCs), muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. Samples may be obtained before treatment, before diagnosis, during treatment, after treatment, or after diagnosis, or a combination thereof.

As used herein, the term "selectable marker" or "selectable marker gene" refers to the use of a gene which encodes an enzymatic activity that confers the ability to grow in medium lacking what would otherwise be an essential nutrient (e.g., the TRPI gene in yeast cells), and/or confer upon the cell resistance to an antibiotic or drug in which the selectable marker is expressed. Selection markers may provide a means to select for or against growth of cells which have been successfully transformed with a vector containing the selection marker sequence and express the marker. A selectable marker may be used to confer a particular phenotype upon a host cell. When a host cell must express a selectable marker to grow in selective medium, the marker is said to be a positive selectable marker (e.g., drug or antibiotic resistance genes which confer the ability to grow in the presence of the appropriate antibiotic, or enable cells to detoxify an exogenously added drug that would otherwise kill the cell). Another example of a positive selection marker is a an auxotrophic marker, which allows cells to synthesize an essential component (usually an amino acid) while grown in media which lacks that essential component. Selectable auxotrophic gene sequences include, for example, hisD, which allows growth in histidine free media in the presence of histidinol. Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers. In some embodiments, selectable markers include resistance genes such as antibiotic resistance genes.

"Subject" as used herein can mean an organism that wants or is in need of the herein described compounds or methods. The subject may be a human or a non-human animal. The subject may be a microorganism. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides, respectively.

The terms "transformation" and "transfection" as used herein refer to the introduction of foreign DNA or polynucleotide into prokaryotic or eukaryotic cells. Transformation of prokaryotic cells may be accomplished by a variety of means known to the art including, for example, the treatment of host cells with $CaCl_2$ to make competent cells, electroporation, etc. Transfection of eukaryotic cells may be accomplished by a variety of means known to the art including, for example, calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof. In some embodiments, variants include homologues. Homologues may be polynucleotides or polypeptides or genes inherited in two species by a common ancestor.

As used herein, the term "vector" is used in reference to a polynucleotide that transfers polynucleotide segment(s) from one cell to another. A vector may also be referred to as a "vehicle" and is a type of "polynucleotide construct" or "nucleic acid construct." Vectors include circular nucleic acid constructs such as plasmids, cosmids, etc., as well as linear nucleic acid constructs (e.g., lambda, phage constructs, PCR products), viruses, and other mediums. A vector may include expression signals such as a promoter and/or an enhancer, and in such a case it is referred to as an expression vector. The term "expression vector" as used herein refers to a polynucleotide molecule containing a desired coding sequence and appropriate polynucleotide sequences necessary for the expression of the operably linked coding sequence in a particular host organism. The expression vector can be transfected and into an organism to express a gene. The expression vector may be recombinant. A polynucleotide sequence for encoding a desired protein can be inserted or introduced into an expression vector. A vector may include polynucleotide sequences to promote or control expression in prokaryotes such as a promoter, an operator (optional), and a ribosome binding site, and other sequences. A vector may include polynucleotide sequences to promote or control expression in eukaryotes such as a promoter, enhancers, termination signal, and polyadenylation signal.

2. Amoebas

An amoeba is a type of cell or organism which has the ability to alter its shape, primarily by extending and retracting pseudopods. Pseudopods are bulges of cytoplasm formed by the coordinated action of actin microfilaments pushing out the plasma membrane that surrounds the cell. Amoebas do not form a single taxonomic group; rather, amoebas are found in every major lineage of eukaryotic organisms. Amoebas occur not only among the protozoa, but also in fungi, algae, and animals. Amoebas may be present in freshwater, saltwater, brackish water, or a combination thereof. The size of an amoeba may vary, depending on the species. In some embodiments, the amoeba has a diameter of about 2.0 μm to about 25 cm, about 5 μm to about 50 μm, about 10 μm to about 45 μm, about 12 μm to about 40 μm, about 5 μm to about 1 cm, about 5 μm to about 20 μm, or about 8 μm to about 15 μm.

Amoebas may include, for example, *Naegleria fowleri* ("brain-eating amoeba"), *Naegleria gruberi, Acanthamoeba* spp. such as *Acanthamoeba castellanii, Balamuthia* ssp. such as *Balamuthia mandrillaris, Entamoeba* ssp. such as *Entamoeba histolytica, Entamoeba coli, Entamoeba dispar, Entamoeba gingivalis*, and *Entamoeba hartmanni, Endolimax nana, Hartmannella vermiformis*, and *Dictyostelium discoideum*. In some embodiments, the amoebas may be described as protozoan parasites.

Diseases caused by amoebas include, for example, amebic encephalitis, meningoencephalitis such as primary amoebic meningoencephalitis (PAM; also known as naegleriasis) and granulomatous amoebic meningoencephalitis, amoebic keratitis, cutaneous amoebiasis, and amoebiasis (amoebic dysentery). In some embodiments, amoebic keratitis causes blindness. In some embodiments, amoebic keratitis particularly affects subjects wearing contact lenses. *E. dispar* and *E. histolytica* may cause amoebiasis. *N. fowleri* may cause PAM. *Acanthamoeba* spp. may cause amoebic keratitis, cutaneous amoebiasis, and/or encephalitis. *B. mandrillaris* may cause granulomatous amoebic meningoencephalitis.

a. *Naegleria fowleri*

In some embodiments, the amoeba is *N. fowleri. N. fowleri* is a free-living amoeba that may be found in warm fresh water, such as ponds, lakes, rivers, and hot springs. *N. fowleri* may also be found in the soil near warm-water discharges of industrial plants, or in unchlorinated or minimally-chlorinated swimming pools. *N. fowleri* occurs in three forms as a cyst, a trophozoite (ameboid), and a biflagellate (it has two flagella). *N. fowleri* does not form a cyst in human tissue. *N. fowleri* may be found in human tissue as the amoeboid trophozoite stage. *N. fowleri* may also be found in the flagellate form in the cerebrospinal fluid. The trophozoite stage can transition to the more mobile flagellate stage if pH or osmolarity changes occur surrounding the subject, or it can encyst if the environment becomes depleted of nutrients, cold, or dry (soil) to survive the unfavorable conditions. *N. fowleri* is infective in the trophozoite stage. Infections most often occur when water containing *N. fowleri* is inhaled through the nose of the subject, where it then enters the nasal and olfactory nerve tissue, traveling to the brain through the cribriform plate. The penetration of the nasal mucosa and subsequent migration and infection of the brain through the olfactory lobe can result in PAM. *N. fowleri* normally eat bacteria, but during human infections, the trophozoites can consume astrocytes and neurons.

3. Expression Vector

Provided herein is an expression vector. The expression vector may be used to transfect an amoeba. In some embodiments, the expression vector is referred to as an amoebic transfection vector. In some embodiments, the expression vector includes a single piece of polynucleotide in linear or circular form. The expression vector may be double-stranded. The expression vectors may contain one or more polynucleotide sequences that generally have some function in the replication, maintenance, or integrity of the vector, such as, for example, origins of replication, as well as one or more selectable marker genes. The expression vector may include a promoter from a protein-encoding gene from an amoeba, a selection marker, and a nucleic acid sequence encoding a polypeptide of interest. The expression vector may also include sequences for a poly(A) site, a multiple cloning site (MCS), a gene encoding a fluorescent protein, or a combination thereof. A polynucleotide sequence of the expression vector may be operably linked to another polynucleotide sequence in the expression vector using conventional recombinant DNA techniques. Suitable techniques are described in Sambrook, J. et al., (1989) "Molecular Cloning. A Laboratory Manual", second edition, Cold Spring Harbor Laboratory Press: Cold Spring Harbor, N.Y., incorporated herein by reference. A polynucleotide sequence can be linked directly to other flanking sequence(s) or can be linked via intervening nucleotides. Intervening polynucleotide sequences of about 0 to about 100 nucleotides, or about 0 to about 20 nucleotides, may be present in between sequences of the vector. For example, in some embodiments, an intervening polynucleotide of 9 nucleotides may be present in between the MCS and the gene encoding a fluorescent protein of the vector.

In some embodiments, the selection marker is positioned downstream of the promoter. In some embodiments, the selection marker is positioned downstream of the promoter and upstream of the poly(A) site. In some embodiments, the promoter is upstream of the MCS. In some embodiments, the promoter, poly(A) site, and selection marker are upstream of the MCS. In some embodiments, the vector comprises a polynucleotide sequence of SEQ ID NO: 7.

a. Promoter

The expression vector may include a promoter. As used herein, "promoter" refers to a part of polynucleotide sequence where transcription regulatory factors bind to direct expression of a gene. In some embodiments, a promoter capable of inducing efficient and stable gene expression can be used to increase gene expression level. A promoter may be "inducible", initiating transcription in response to an inducing agent or, in contrast, a promoter may be "constitutive", whereby an inducing agent does not regulate the rate of transcription. The promoter may be regulatable. For example, a regulatable promoter may include an inducible promoter. In some embodiments, the promoter is an inducible promoter. In some embodiments, the promoter is a constitutive promoter. The promoter may be from a gene that is constitutively expressed in all stages of an amoeba. In some embodiments, the promoter is from a gene from an amoeba of the genus *Naegleria*. In some embodiments, the promoter is from a gene from *N. fowleri*. The promoter may be from a protein-coding gene from an amoeba. In some embodiments, the promoter is from a gene coding for actin, tubulin, or ribosomal RNA in an amoeba. In some embodiments, the promoter is from the ACT1 gene. In some embodiments, the promoter is from the ACT1 gene of an amoeba of the genus *Naegleria*. In some embodiments, the promoter is from the ACT1 gene from *N. fowleri*. In some embodiments, the promoter comprises a polynucleotide sequence of SEQ ID NO: 4.

b. Selection Markers

The expression vector may include at least one selection marker. In some embodiments, the selection marker is selected from hygromycin, puromycin, noursecothricin, and bleomycin resistance genes, or a combination thereof. A vector may include a single selection marker. A vector may include multiple different selection markers. A plurality of vectors may include multiple different selection markers, each vector including one or more selection markers. Multiple selection markers may be used, for example, to facilitate multiple rounds of transfection, different genes being expressed, multiple genes being knocked out, or a combination thereof. In some embodiments, the vector includes a hygromycin resistance gene. In some embodiments, the hygromycin resistance gene comprises a polynucleotide sequence of SEQ ID NO: 6.

c. Poly(A) Site

The expression vector may include a poly(A) site. As used herein, "poly(A) site" may also be referred to as polyA tail, polyA signal, polyA, polyadenylic acid, or polyadenylic acid tail, and it refers to a polynucleotide sequence that directs both the termination and polyadenylation of the nascent RNA transcript. The poly(A) site may include a plurality of adenine nucleotides, such as a consecutive sequence of adenine nucleotides. Poly(A) sites are normally present at the 3' terminal of mRNA of eukaryotic cells. Efficient polyadenylation of the recombinant transcript is desirable as transcripts lacking a poly(A) site may be unstable and rapidly degraded. The poly(A) site utilized in an expression vector may be "heterologous" or "endogenous." An endogenous poly(A) site is one that is found naturally at the 3' end of the coding region of a given gene in the genome. A heterologous poly(A) site is one which is one which is isolated from one gene and placed 3' of another gene. The length of a poly(A) site may be, for example, 10 to 200 nucleotides, or 50 to 150 nucleotides. Poly(A) tail is normally involved in stabilization, translation, and transport of mRNA from the nucleus to cytoplasm. Poly(A) tail may direct both the termination and polyadenylation of the nascent RNA transcript. Efficient polyadenylation of the recombinant transcript may be desirable as transcripts lacking a poly(A) tail may be unstable and/or rapidly degraded. The poly(A) site utilized in an expression vector may be "heterologous" or "endogenous." Examples of poly(A) sites and a description thereof may be found in Sambrook et al., Molecular Cloning: A Laboratory Manual, Cold Spring Harbor (1989), incorporated herein by reference. In some embodiments, the poly(A) site comprises a polynucleotide sequence of SEQ ID NO: 5. Efficient expression of recombinant DNA sequences in eukaryotic cells may require the expression of signals directing the efficient termination and polyadenylation of the resulting transcript. Transcription termination signals are generally found downstream of the polyadenylation signal and may be a few hundred nucleotides in length.

d. Multiple Cloning Site (MCS)

The expression vector may include a multiple cloning site (MCS). The MCS may also be referred to as a "polylinker." The term "multiple cloning site" refers to a polynucleotide sequence comprising restriction sites for the purpose of cloning polynucleotide fragments into an expression vector. The MCS may be used for the insertion and/or excision of polynucleotide sequences such as the coding region of a gene. In some embodiments, the vector includes a MCS comprising a polynucleotide sequence of SEQ ID NO: 2. In some embodiments, the vector includes a MCS comprising a polynucleotide sequence of SEQ ID NO: 3. In some embodiments, the vector does not include a cytomegalovirus (CMV) promoter.

e. Polypeptide of Interest

The expression vector may include a nucleic acid sequence encoding a polypeptide of interest, operably linked to the promoter. In some embodiments, the polypeptide of interest comprises an affinity tag for purification. In some embodiments, the polypeptide of interest comprises a fluorescent protein.

i) Fluorescent Protein

In some embodiments, the vector comprises a polynucleotide encoding a fluorescent protein. The polypeptide of interest may comprise a fluorescent protein. A fluorescent protein may be in addition to the polypeptide of interest. The vector may encode a fusion protein comprising a protein of interest and a fluorescent protein. The polynucleotide encoding a fluorescent protein may be operably linked to the promoter and to the polypeptide of interest.

Fluorescent proteins include, for example, Aequorea-derived proteins such as Green Fluorescent Protein (GFP), Enhanced Green Fluorescent Protein ("EGFP"), Yellow Fluorescent Protein ("YFP"), and Cyan Fluorescent Protein ("CFP"), as well as proteins derived from coral species including, but not limited to, *Discosoma* and *Trachyphyllia geoffroyi*. Other proteins having fluorescent or other signaling properties can also be used. Specific examples of fluorescent proteins (and their encoding nucleic acids) are well known in the art including, without limitation, those reported as Genbank Accession Nos. AB195239, DD431502-DD431504, DD420089-DD420091, AY013821, AY013824-AY013827, EF064258-EF064259, AF435-427-AF435-434, DQ092360-DQ092365, DQ525024-DQ525025, X83959-X83960, AY533296, AB041904, X96418, BD136947-BD136949, U73901, AX250563-AX250571, AF302837, AF183395, AF058694-AF058695, U50963, L29345, M62653-M62654, DQ301560, AY679106-AY679108, AY678264-AY678271, AF168419-AF168420, AF272711, AY786536-AY786537, AF545828, AF506025-AF506027, AF420593, BAC20344, BD440518-BD440519, and AB085641, each of which is hereby incorporated by reference in its entirety. In some embodiments, the fluorescent protein comprises GFP. In some embodiments, the fluorescent protein comprises EGFP. EGFP may comprise a polypeptide having an amino acid sequence of SEQ ID NO: 8. EGFP may comprise a polypeptide encoded by a polynucleotide sequence of SEQ ID NO: 9.

4. Transfection

Further provided herein is an amoeba transfected with an expression vector as detailed herein. In some embodiments, the amoeba transfected with an expression vector as detailed herein has reduced virulence compared to a control amoeba. The control may be an untransformed amoeba or an amoeba transformed with a different vector.

An amoeba may be transfected with an expression vector as detailed herein according to any suitable means known by those of skill in the art. In some embodiments, an amoeba may be transfected with an expression vector by electroporation.

Host cells which are transfected with the vector as detailed herein can be screened using conventional techniques. For example, when the gene to be expressed is a gene which confers resistance to a particular antibiotic, screening can be accomplished by gradually or immediately increasing the concentration of that particular antibiotic.

Confirmation that gene knockout or gene complementation has occurred can be obtained by Southern blots of restriction enzyme-digested DNA from the transformed amoeba.

Further provided herein is an amoeba transfected with an expression vector as detailed herein. In some embodiments, the transfected amoeba is less virulent than the wild-type amoeba.

5. Vaccine

Further provided herein is a vaccine comprising an amoeba transfected with an expression vector as detailed herein. A transformed or transfected amoeba may be used to generate vaccines against amoeba-mediated diseases. If the transformed amoeba is less virulent than wild-type, the transformed microorganisms can be used as "modified" forms. Conventional techniques can be used to generate live vaccines using the modified forms of the amoeba. Alternatively, the transformed amoeba can be destroyed and used to formulate killed vaccines using conventional techniques. In yet another embodiment, polypeptides or fragments thereof from the transformed amoeba can be isolated and formulated into synthetic vaccines using conventional techniques. The vaccine may be administered to a subject to treat or prevent a disease.

6. Methods a. Methods of Expressing a Foreign Protein in an Amoeba

Provided herein are methods of expressing a polypeptide of interest in an amoeba. The method may include transforming an amoeba with the expression vector detailed herein, isolating the transformed amoeba, and expressing the polypeptide of interest in the amoeba. The polypeptide of interest may be a foreign protein. The polypeptide of interest may comprise the foreign protein.

In some embodiments, the transforming is performed by electroporation. In some embodiments, the isolating comprises culturing the amoeba in the presence of the antibiotic of the antibiotic resistance gene, such as hygromycin, puromycin, nourseothricin, or bleomycin, or a combination thereof. The polypeptide of interest may be expressed during culturing of the amoeba. The polypeptide of interest may be expressed from a constitutive promoter. The polypeptide of interest may be expressed during culturing of the amoeba and independent of the influence of regulation. The polypeptide of interest may be expressed from a regulatable promoter. The regulatable promoter may be inducible. Transcription of the polynucleotide encoding the polypeptide of interest may be initiated in response to addition of an inducing agent at any time point to the culture media. The inducing agent may be specific for the inducible promoter. The inducing agent may be added to the culture at the beginning of culturing the amoeba, after 1 hour, after 2 hours, after 3 hours, after 4 hours, after 5 hours, after 12 hours, after 24 hours, after 2 days, after 3 days, after 4 days, after 1 week, or after 3 weeks of culturing the amoeba.

b. Methods of Manipulating an Amoeba Genome

Provided herein are methods of manipulating an amoeba genome. The method may include transforming the amoeba with the expression vector detailed herein, isolating the transformed amoeba, and expressing the polypeptide of interest in the amoeba. The polypeptide of interest may be a foreign protein. The polypeptide of interest may comprise the foreign protein.

In some embodiments, the transforming is performed by electroporation. In some embodiments, the isolating comprises culturing the amoeba in the presence of the antibiotic of the antibiotic resistance gene, such as hygromycin, puromycin, nourseothricin, or bleomycin, or a combination thereof. The polypeptide of interest may be expressed during culturing of the amoeba. The polypeptide of interest may be expressed from a constitutive promoter. The polypeptide of interest may be expressed during culturing of the amoeba and independent of the influence of regulation. The polypeptide of interest may be expressed from a regulatable promoter. The regulatable promoter may be inducible. Transcription of the polynucleotide encoding the polypeptide of interest may be initiated in response to addition of an inducing agent at any time point to the culture media. The inducing agent may be specific for the inducible promoter. The inducing agent may be added to the culture at the beginning of culturing the amoeba, after 1 hour, after 2 hours, after 3 hours, after 4 hours, after 5 hours, after 12 hours, after 24 hours, after 2 days, after 3 days, after 4 days, after 1 week, or after 3 weeks of culturing the amoeba.

7. Examples

Example 1

Screening of Selection Markers

Preliminary experiments revealed that *N. fowleri* has natural resistance to neomycin. Five different selection markers were screened for their suitability to use in an *N. fowleri* transfection system. MTS viability assays in *N. fowleri* revealed $IC_{50}$ values of neomycin for 681 pg/m L, 1.4 pg/mL for hygromycin, 0.6 pg/mL for puromycin, 0.5 pg/mL for bleomycin, and 27 pg/mL for nourseothricin (TABLE 1 and FIG. 1). The results indicated that hygromycin, puromycin, bleomycin, and nourseothricin would be suitable independent selection markers for *N. fowleri*. Hygromycin was used in subsequent studies as the selectable marker, partly due to its easy use in other eukaryotic transfection systems.

TABLE 1

Results from MTS viability assays in *N. fowleri*.

| | Neo | Hyg | Puro | Ble | Nst |
|---|---|---|---|---|---|
| $IC_{50}$ Value | 681.1 | 1.38 | 0.58 | 0.49 | 26.5 |
| $IC_{90}$ Value | 2385.3 | 5.59 | 1.49 | 1.62 | 165.4 |
| $IC_{95}$ Value | 3078.4 | 7.31 | 1.91 | 2.10 | 218.7 |

Example 2

Generation of a *Naegleria*-Specific Transfection Vector

Figure 2A:
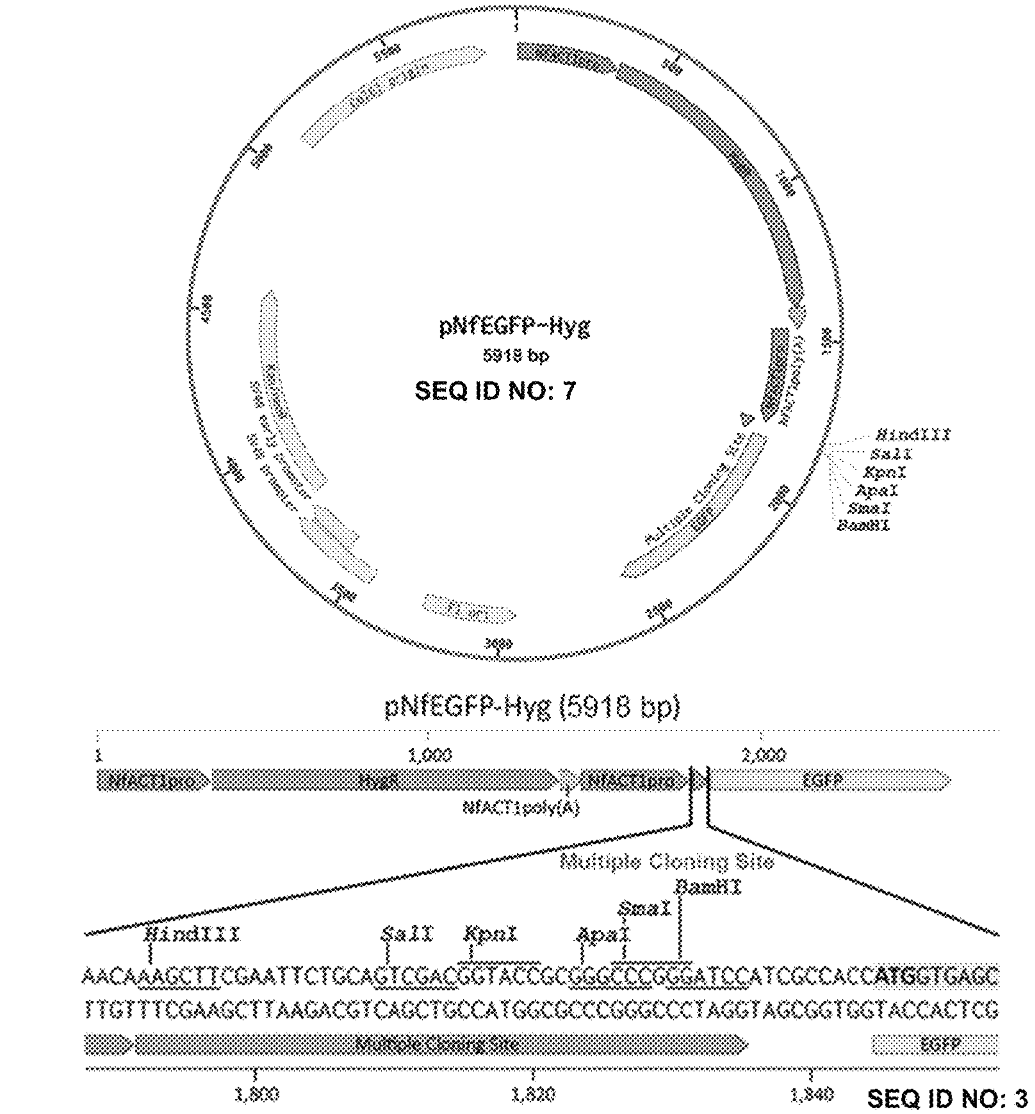
FIG. 2A is a schematic diagram of the pNfEGFP-Hyg vector and the multiple cloning site (MCS).
Figure 5:
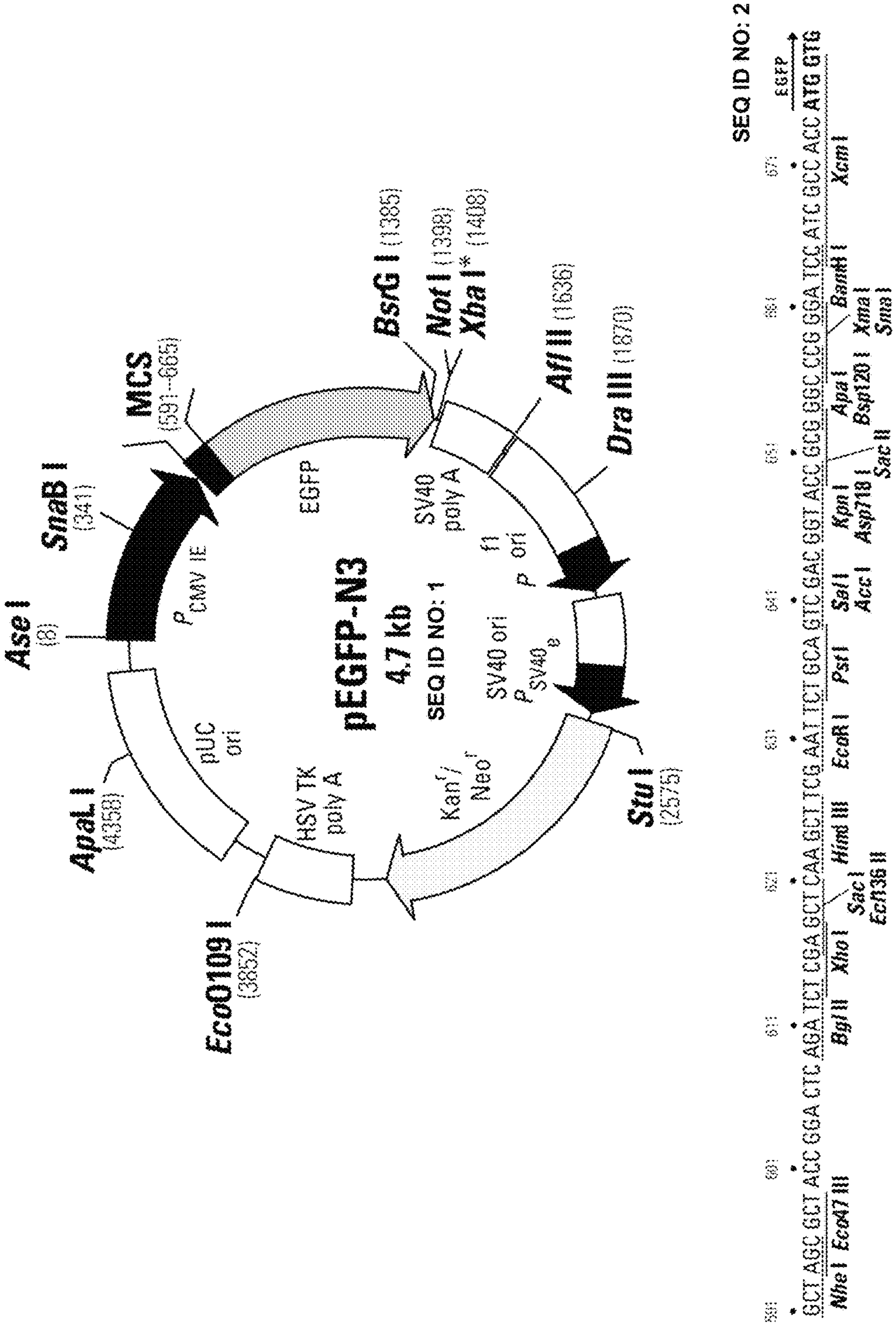
FIG. 5 is a schematic diagram of the pEGFP-N3 vector and the multiple cloning site (MCS).

A *Naegleria*-specific transfection vector was engineered using the pEGFP-N3 mammalian vector (Clontech, Mountain View, Calif.; catalog number 6080-1; FIG. 5; SEQ ID NO: 1) as a backbone. The CMV promoter was replaced with the *N. fowleri* actin (ACT1) promoter (SEQ ID NO: 4) immediately upstream of the multiple cloning site (MCS; SEQ ID NO: 2; 591-665 nt of SEQ ID NO: 1) (FIG. 2A). This orientation of elements would also facilitate the expression of EGFP-tagged proteins. The hygromycin resistance gene (SEQ ID NO: 6) was also introduced into the vector. The hygromycin resistance gene ($Hyg^R$; SEQ ID NO: 6) was flanked by the promoter region (SEQ ID NO: 4) and polyadenylation site (SEQ ID NO: 5) of the constitutively expressed *N. fowleri* beta-actin gene. The *N. fowleri* beta-actin ACT1 promoter (SEQ ID NO: 4) includes a TATA box motif (TATA (A/T) A (A/T) (A/G)) and six CAAT box motifs (e.g., CCAAT and ATTGG) for transcriptional regulation. The consensus motifs are underlined and the transcription start site is indicated in FIG. 2B, as identified from mRNA sequence analysis. The ACT1 3' untranslated region of the poly(A) site (SEQ ID NO: 5) that contains the poly(A) signal motif (AATAAA, underlined, yellow) and the poly(A) site (TA, underlined, red) was identified from mRNA sequence analysis. The ACT1 3' untranslated region of the poly(A) site (SEQ ID NO: 5) is followed by a GT-rich downstream element (underlined, teal; SEQ ID NO: 10) to enhance polyadenylation, as identified from gDNA sequence analysis. The result was the novel pNfEGFP-Hyg transfection vector (SEQ ID NO: 7; FIG. 2B).

Example 3

Quantification of EGFP Expression in *Naegleria*

*N. fowleri* amoebae were transfected with the pNfEGFP-Hyg vector (detailed in Example 2) by electroporation. Transfection was performed by electroporation (BioRad GenePulser Xcell™ with 500 pF, 200V and ∞ ohm electroporation conditions). Transfectants were selected by growing in the presence of 20 to 40 μg/mL hygromycin.

Figure 3:
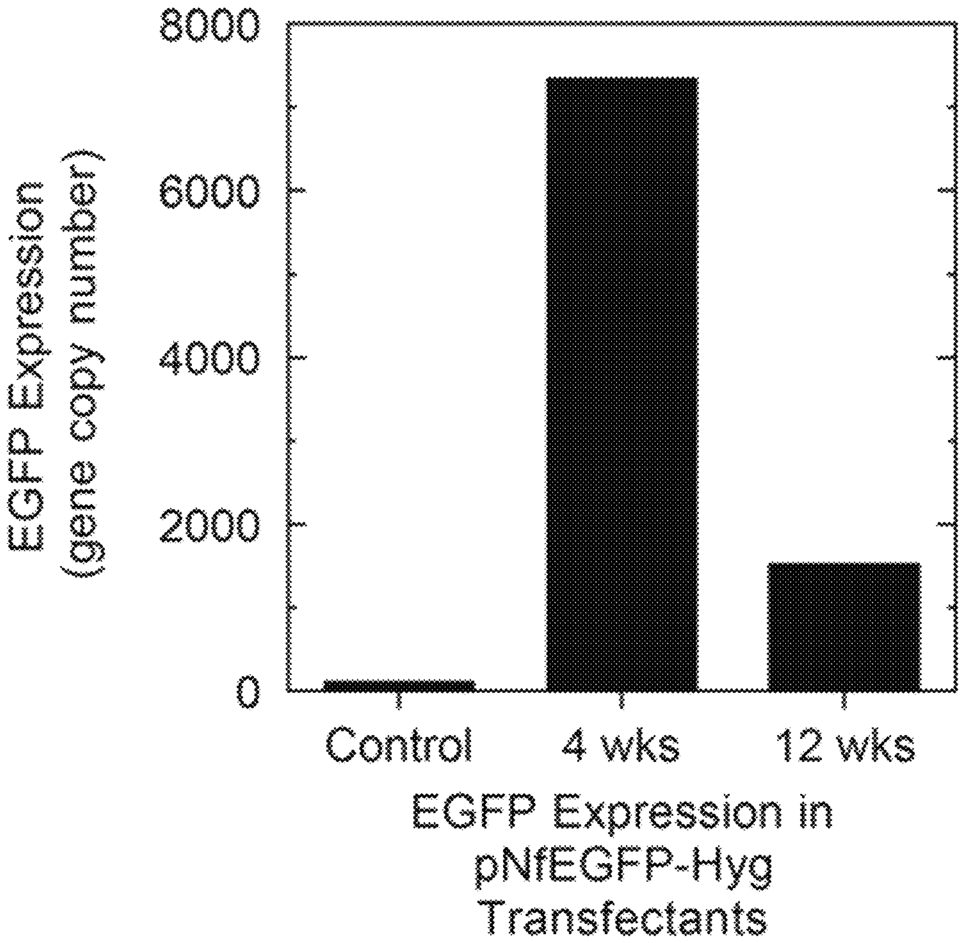
FIG. 3 is a graph of EGFP expression in pNfEGFP-Hyg transfectants at 4 weeks and 12 weeks.

Transfectants were grown for 4 weeks or 12 weeks in 40 μg/mL hygromycin. Total DNA was isolated from the *Naegleria*. Quantitative PCR was used to measure the presence of EGFP DNA and hence demonstrated continuous expression of pNfEGFPHyg vector DNA in *N. fowleri* transfectants (FIG. 3). Untransfected amebae served as control. *N. fowleri* actin gene was used as internal standard.

Figure 4:
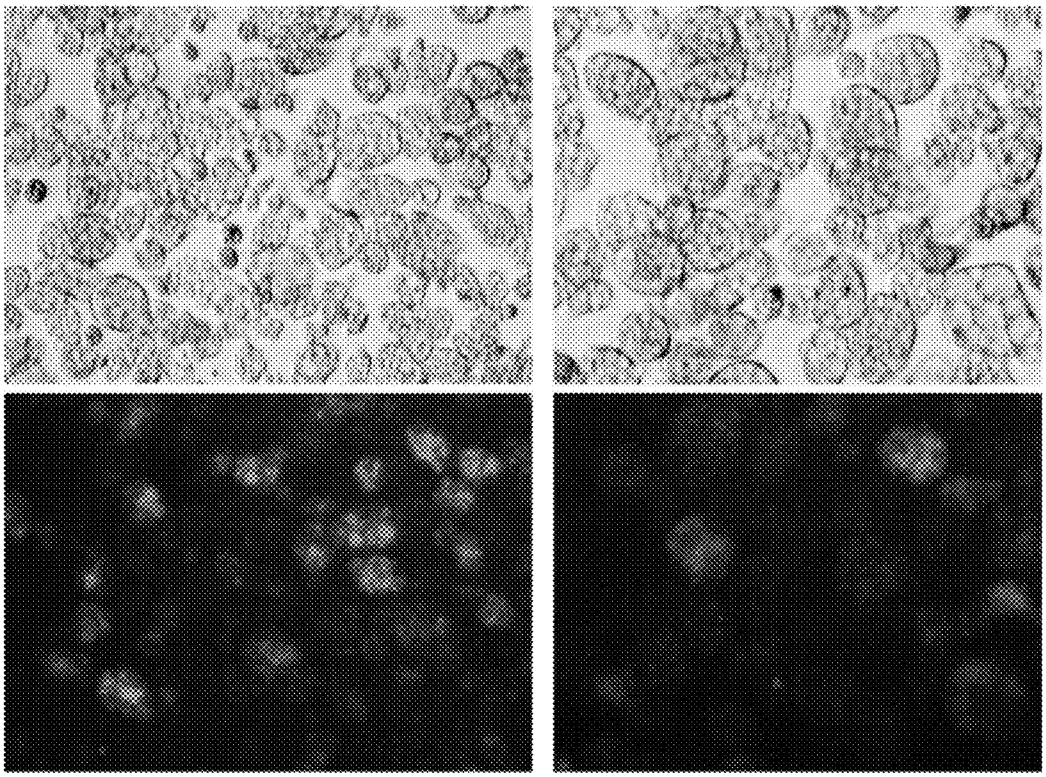
FIG. 4 are images of *Naegleria fowleri* transfected with pNfEGFP-Hyg vector.

Expression of enhanced green fluorescence protein (EGFP) in transfected amoebae after 10 weeks of hygromycin selection (40 μg/mL) was examined with microscopy. The results confirmed the quantitative PCR results and demonstrated stable expression of EGFP from the pNfEGFP-Hyg vector in transfected *Naegleria*. Results are shown in FIG. 4. The top two images of FIG. 4 are with phase contrast light microscopy. The bottom two images of FIG. 4 are the corresponding EGFP fluorescence microscopy images of live amoebae. EGFP protein by itself, without tagging to another protein of interest (which the multiple cloning site of pNfEGFPHyg permits as an option) was concentrated in digestive vacuoles of the live amoebae.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. An expression vector comprising: a promoter from a protein-encoding gene from an amoeba; a selection marker selected from hygromycin resistance gene, puromycin resistance gene, nourseothricin resistance gene, and bleomycin resistance gene; and a nucleic acid sequence encoding a polypeptide of interest, operably linked to the promoter.

Clause 2. The vector of clause 1, wherein the amoeba is *N. fowleri.*

Clause 3. The vector of clause 1 or 2, wherein the promoter is from the ACT1 gene from *N. fowleri.*

Clause 4. The vector of clause 3, wherein the promoter comprises a polynucleotide sequence of SEQ ID NO: 4.

Clause 5. The vector of any one of clauses 1-4, wherein the vector further comprises a poly(A) site, operably linked to the promoter.

Clause 6. The vector of clause 5, wherein the poly(A) site comprises a polynucleotide sequence of SEQ ID NO: 5.

Clause 7. The vector of any one of clauses 5-7, wherein the selection marker is positioned downstream of the promoter and upstream of the poly(A) site.

Clause 8. The vector of any one of clauses 1-7, wherein the selection marker comprises the hygromycin resistance gene.

Clause 9. The vector of clause 8, wherein the hygromycin resistance gene comprises a polynucleotide sequence of SEQ ID NO: 6.

Clause 10. The vector of any one of clauses 1-9, wherein the vector does not include a cytomegalovirus (CMV) promoter.

Clause 11. The vector of any one of clauses 1-10, wherein the vector further comprises a multiple cloning site (MCS), and wherein the promoter is upstream of the MCS.

Clause 12. The vector of clause 11, wherein the promoter, poly(A) site, and selection marker are upstream of the MCS.

Clause 13. The vector of any one of clauses 11-12, wherein the MCS comprises a polynucleotide sequence of SEQ ID NO: 3.

Clause 14. The vector of any one of clauses 1-13, wherein the vector further comprises a polynucleotide encoding a fluorescent protein.

Clause 15. The vector of clause 14, wherein the polynucleotide encoding a fluorescent protein is operably linked to the promoter and to the polypeptide of interest.

Clause 16. The vector of any one of clauses 1-15, wherein the vector comprises a polynucleotide sequence of SEQ ID NO: 7.

Clause 17. An amoeba transformed with the vector of any one of clauses 1-16.

Clause 18. The amoeba of clause 17, wherein the amoeba has reduced virulence compared to a control amoeba.

Clause 19. The amoeba of clause 18, wherein the control comprises an untransformed amoeba or an amoeba transformed with a different vector.

Clause 20. A vaccine comprising the amoeba of any one of clauses 17-19.

Clause 21. A method of expressing a foreign protein in an amoeba, the method comprising: transforming an amoeba with the vector of any one of clauses 1-16, wherein the polypeptide of interest comprises the foreign protein; isolating the transformed amoeba; and expressing the foreign protein in the amoeba.

Clause 22. A method of manipulating an amoeba genome, the method comprising: transforming the amoeba with the vector of any one of clauses 1-16; isolating the transformed amoeba; and expressing the polypeptide of interest in the amoeba.

Clause 23. The method of clause 21 or 22, wherein the transforming is performed by electroporation.

Clause 24. The method of any one of clauses 21-23, wherein the isolating comprises culturing the amoeba in the presence of hygromycin, puromycin, nourseothricin, or bleomycin, or a combination thereof.

SEQUENCES pEGFP-N3 mammalian vector (4729 nt)

SEQ ID NO: 1

TAGTTATTAATAGTAATCAATTACGGGGTCATTAGTTCATAGCCCATATATGGAG

TTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGAC

TTTCCATTGACGTCAATGGGTGGAGTATTTACGGTAAACTGCCCACTTGGCAGTA

CATCAAGTGTATCATATGCCAAGTACGCCCCCTATTGACGTCAATGACGGTAAAT

GGCCCGCCTGGCATTATGCCCAGTACATGACCTTATGGGACTTTCCTACTTGGCA

GTACATCTACGTATTAGTCATCGCTATTACCATGGTGATGCGGTTTTGGCAGTAC

ATCAATGGGCGTGGATAGCGGTTTGACTCACGGGGATTTCCAAGTCTCCACCCCA

TTGACGTCAATGGGAGTTTGTTTTGGCACCAAAATCAACGGGACTTTCCAAAATG

TCGTAACAACTCCGCCCCATTGACGCAAATGGGCGGTAGGCGTGTACGGTGGGAG

GTCTATATAAGCAGAGCTGGTTTAGTGAACCGTCAGATCCGCTAGCGCTACCGGA

CTCAGATCTCGAGCTCAAGCTTCGAATTCTGCAGTCGACGGTACCGCGGGCCCGG

GATCCATCGCCACCATGGTGAGCAAGGGCGAGGAGCTGTTCACCGGGGTGGTGCC

CATCCTGGTCGAGCTGGACGGCGACGTAAACGGCCACAAGTTCAGCGTGTCCGGC

GAGGGCGAGGGCGATGCCACCTACGGCAAGCTGACCCTGAAGTTCATCTGCACCA

CCGGCAAGCTGCCCGTGCCCTGGCCCACCCTCGTGACCACCCTGACCTACGGCGT

GCAGTGCTTCAGCCGCTACCCCGACCACATGAAGCAGCACGACTTCTTCAAGTCC

GCCATGCCCGAAGGCTACGTCCAGGAGCGCACCATCTTCTTCAAGGACGACGGCA

ACTACAAGACCCGCGCCGAGGTGAAGTTCGAGGGCGACACCCTGGTGAACCGCAT

CGAGCTGAAGGGCATCGACTTCAAGGAGGACGGCAACATCCTGGGGCACAAGCTG

GAGTACAACTACAACAGCCACAACGTCTATATCATGGCCGACAAGCAGAAGAACG

GCATCAAGGTGAACTTCAAGATCCGCCACAACATCGAGGACGGCAGCGTGCAGCT

CGCCGACCACTACCAGCAGAACACCCCCATCGGCGACGGCCCCGTGCTGCTGCCC

GACAACCACTACCTGAGCACCCAGTCCGCCCTGAGCAAAGACCCCAACGAGAAGC

GCGATCACATGGTCCTGCTGGAGTTCGTGACCGCCGCCGGGATCACTCTCGGCAT

GGACGAGCTGTACAAGTAAAGCGGCCGCGACTCTAGATCATAATCAGCCATACCA

CATTTGTAGAGGTTTTACTTGCTTTAAAAAACCTCCCACACCTCCCCCTGAACCT

GAAACATAAAATGAATGCAATTGTTGTTGTTAACTTGTTTATTGCAGCTTATAAT

GGTTACAAATAAAGCAATAGCATCACAAATTTCACAAATAAAGCATTTTTTTCAC

TGCATTCTAGTTGTGGTTTGTCCAAACTCATCAATGTATCTTAAGGCGTAAATTG

TAAGCGTTAATATTTTGTTAAAATTCGCGTTAAATTTTTGTTAAATCAGCTCATT

TTTTAACCAATAGGCCGAAATCGGCAAAATCCCTTATAAATCAAAAGAATAGACC

GAGATAGGGTTGAGTGTTGTTCCAGTTTGGAACAAGAGTCCACTATTAAAGAACG

TGGACTCCAACGTCAAAGGGCGAAAAACCGTCTATCAGGGCGATGGCCCACTACG

-continued

TGAACCATCACCCTAATCAAGTTTTTTGGGGTCGAGGTGCCGTAAAGCACTAAAT

CGGAACCCTAAAGGGAGCCCCCGATTTAGAGCTTGACGGGGAAAGCCGGCGAACG

TGGCGAGAAAGGAAGGGAAGAAAGCGAAAGGAGCGGGCGCTAGGGCGCTGGCAAG

TGTAGCGGTCACGCTGCGCGTAACCACCACACCCGCCGCGCTTAATGCGCCGCTA

CAGGGCGCGTCAGGTGGCACTTTTCGGGGAAATGTGCGCGGAACCCCTATTTGTT

TATTTTTCTAAATACATTCAAATATGTATCCGCTCATGAGACAATAACCCTGATA

AATGCTTCAATAATATTGAAAAAGGAAGAGTCCTGAGGCGGAAAGAACCAGCTGT

GGAATGTGTGTCAGTTAGGGTGTGGAAAGTCCCCAGGCTCCCCAGCAGGCAGAAG

TATGCAAAGCATGCATCTCAATTAGTCAGCAACCAGGTGTGGAAAGTCCCCAGGC

TCCCCAGCAGGCAGAAGTATGCAAAGCATGCATCTCAATTAGTCAGCAACCATAG

TCCCGCCCCTAACTCCGCCCATCCCGCCCCTAACTCCGCCCAGTTCCGCCCATTC

TCCGCCCCATGGCTGACTAATTTTTTTTATTTATGCAGAGGCCGAGGCCGCCTCG

GCCTCTGAGCTATTCCAGAAGTAGTGAGGAGGCTTTTTTGGAGGCCTAGGCTTTT

GCAAAGATCGATCAAGAGACAGGATGAGGATCGTTTCGCATGATTGAACAAGATG

GATTGCACGCAGGTTCTCCGGCCGCTTGGGTGGAGAGGCTATTCGGCTATGACTG

GGCACAACAGACAATCGGCTGCTCTGATGCCGCCGTGTTCCGGCTGTCAGCGCAG

GGGCGCCCGGTTCTTTTTGTCAAGACCGACCTGTCCGGTGCCCTGAATGAACTGC

AAGACGAGGCAGCGCGGCTATCGTGGCTGGCCACGACGGGCGTTCCTTGCGCAGC

TGTGCTCGACGTTGTCACTGAAGCGGGAAGGGACTGGCTGCTATTGGGCGAAGTG

CCGGGGCAGGATCTCCTGTCATCTCACCTTGCTCCTGCCGAGAAAGTATCCATCA

TGGCTGATGCAATGCGGCGGCTGCATACGCTTGATCCGGCTACCTGCCCATTCGA

CCACCAAGCGAAACATCGCATCGAGCGAGCACGTACTCGGATGGAAGCCGGTCTT

GTCGATCAGGATGATCTGGACGAAGAGCATCAGGGGCTCGCGCCAGCCGAACTGT

TCGCCAGGCTCAAGGCGAGCATGCCCGACGGCGAGGATCTCGTCGTGACCCATGG

CGATGCCTGCTTGCCGAATATCATGGTGGAAAATGGCCGCTTTTCTGGATTCATC

GACTGTGGCCGGCTGGGTGTGGCGGACCGCTATCAGGACATAGCGTTGGCTACCC

GTGATATTGCTGAAGAGCTTGGCGGCGAATGGGCTGACCGCTTCCTCGTGCTTTA

CGGTATCGCCGCTCCCGATTCGCAGCGCATCGCCTTCTATCGCCTTCTTGACGAG

TTCTTCTGAGCGGGACTCTGGGGTTCGAAATGACCGACCAAGCGACGCCCAACCT

GCCATCACGAGATTTCGATTCCACCGCCGCCTTCTATGAAAGGTTGGGCTTCGGA

ATCGTTTTCCGGGACGCCGGCTGGATGATCCTCCAGCGCGGGGATCTCATGCTGG

AGTTCTTCGCCCACCCTAGGGGGAGGCTAACTGAAACACGGAAGGAGACAATACC

GGAAGGAACCCGCGCTATGACGGCAATAAAAAGACAGAATAAAACGCACGGTGTT

GGGTCGTTTGTTCATAAACGCGGGGTTCGGTCCCAGGGCTGGCACTCTGTCGATA

CCCCACCGAGACCCCATTGGGGCCAATACGCCCGCGTTTCTTCCTTTTCCCCACC

CCACCCCCCAAGTTCGGGTGAAGGCCCAGGGCTCGCAGCCAACGTCGGGGCGGCA

GGCCCTGCCATAGCCTCAGGTTACTCATATATACTTTAGATTGATTTAAAACTTC

ATTTTTAATTTAAAAGGATCTAGGTGAAGATCCTTTTTGATAATCTCATGACCAA

AATCCCTTAACGTGAGTTTTCGTTCCACTGAGCGTCAGACCCCGTAGAAAAGATC

AAAGGATCTTCTTGAGATCCTTTTTTTCTGCGCGTAATCTGCTGCTTGCAAACAA

-continued

AAAAACCACCGCTACCAGCGGTGGTTTGTTTGCCGGATCAAGAGCTACCAACTCT

TTTTCCGAAGGTAACTGGCTTCAGCAGAGCGCAGATACCAAATACTGTCCTTCTA

GTGTAGCCGTAGTTAGGCCACCACTTCAAGAACTCTGTAGCACCGCCTACATACC

TCGCTCTGCTAATCCTGTTACCAGTGGCTGCTGCCAGTGGCGATAAGTCGTGTCT

TACCGGGTTGGACTCAAGACGATAGTTACCGGATAAGGCGCAGCGGTCGGGCTGA

ACGGGGGGTTCGTGCACACAGCCCAGCTTGGAGCGAACGACCTACACCGAACTGA

GATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTT

CCAGGGGGAAACGCCTGGTATCTTTATAGTCCTGTCGGGTTTCGCCACCTCTGAC

TTGAGCGTCGATTTTTGTGATGCTCGTCAGGGGGGCGGAGCCTATGGAAAAACGC

CAGCAACGCGGCCTTTTTACGGTTCCTGGCCTTTTGCTGGCCTTTTGCTCACATG

TTCTTTCCTGCGTTATCCCCTGATTCTGTGGATAACCGTATTACCGCCATGCAT

Multiple cloning site (MCS) of pEGFP-N3 vector (from 591-665 nt of the plasmid, 75 nt)

SEQ ID NO: 2

GCTAGCGCTA CCGGACTCAG ATCTCGAGCT CAAGCTTCGA ATTCTGCAGT

CGACGGTACC GCGGGCCCGG GATCC

Multiple cloning site (MCS) of pNfEGFP-Hyg vector (44 nt)

SEQ ID NO: 3

AAGCTTCGAA TTCTGCAGTC GACGGTACCG CGGGCCCGGG ATCC promoter from the ACT1 gene in *N. fowleri* used in pNfEGFP-Hyg vector (335 nt)

SEQ ID NO: 4

CAAGCCTCAT TCTTGAAGTT GTCAATTTGA AAGGGAGAAA TTGTTGGCAT

TTACAGTAAG ACACTTGCTT TCTTTGAGGA TGATCAGACA TCTCTCAGAA

ATGCACACCT TTCATCAAGT GAATGACAAT TTCATTGGGA AGGCAACTTT

CATTTATGGT TTGGGTCATC ATCCATCACT ATCAAGTTTA CAATACATCA

AAAATATCAT TGGTTTGTTG AAGGTCCAGC AACACGTCAC ACCAAATCTT

TAAATTTTTT CAATAATTAT TAACAGCATT CTTTCACACA AACAAAAAAC

TCAACAACAA CTTCCTCTCC AACAAGAACA ACAAA poly(A) site of pNfEGFP-Hyg vector (100 nt)

SEQ ID NO: 5

ATTGACCTTG GATGCACATT ATCAAATTCC ATTGTAATAA AACATAAAAT

CTATGTAAAA TCATGCATGA GTTGTGTCTT TGTAAAATTG ATTTGTAGTC hygromycin resistance gene, including ATG start codon and TAG stop codon (1026 nt)

SEQ ID NO: 6

ATGAAAAAGCCTGAACTCACCGCGACGTCTGTCGAGAAGTTTCTGATCGAAAAGT

TCGACAGCGTCTCCGACCTGATGCAGCTCTCGGAGGGCGAAGAATCTCGTGCTTT

CAGCTTCGATGTAGGAGGGCGTGGATATGTCCTGCGGGTAAATAGCTGCGCCGAT

GGTTTCTACAAAGATCGTTATGTTTATCGGCACTTTGCATCGGCCGCGCTCCCGA

TTCCGGAAGTGCTTGACATTGGGGAATTCAGCGAGAGCCTGACCTATTGCATCTC

CCGCCGTGCACAGGGTGTCACGTTGCAAGACCTGCCTGAAACCGAACTGCCCGCT

GTTCTGCAGCCGGTCGCGGAGGCCATGGATGCGATCGCTGCGGCCGATCTTAGCC

AGACGAGCGGGTTCGGCCCATTCGGACCGCAAGGAATCGGTCAATACACTACATG

GCGTGATTTCATATGCGCGATTGCTGATCCCCATGTGTATCACTGGCAAACTGTG

ATGGACGACACCGTCAGTGCGTCCGTCGCGCAGGCTCTCGATGAGCTGATGCTTT

-continued

GGGCCGAGGACTGCCCCGAAGTCCGGCACCTCGTGCACGCGGATTTCGGCTCCAA

CAATGTCCTGACGGACAATGGCCGCATAACAGCGGTCATTGACTGGAGCGAGGCG

ATGTTCGGGGATTCCCAATACGAGGTCGCCAACATCTTCTTCTGGAGGCCGTGGT

TGGCTTGTATGGAGCAGCAGACGCGCTACTTCGAGCGGAGGCATCCGGAGCTTGC

AGGATCGCCGCGGCTCCGGGCGTATATGCTCCGCATTGGTCTTGACCAACTCTAT

CAGAGCTTGGTTGACGGCAATTTCGATGATGCAGCTTGGGCGCAGGGTCGATGCG

ACGCAATCGTCCGATCCGGAGCCGGGACTGTCGGGCGTACACAAATCGCCCGCAG

AAGCGCGGCCGTCTGGACCGATGGCTGTGTAGAAGTACTCGCCGATAGTGGAAAC

CGACGCCCCAGCACTCGTCCGAGGGCAAAGGAATAG pNfEGFP-Hyg vector (5918 bp)

SEQ ID NO: 7

TAGTTATTATGCAAGCCTCATTCTTGAAGTTGTCAATTTGAAAGGGAGAAATTGT

TGGCATTTACAGTAAGACACTTGCTTTCTTTGAGGATGATCAGACATCTCTCAGA

AATGCACACCTTTCATCAAGTGAATGACAATTTCATTGGGAAGGCAACTTTCATT

TATGGTTTGGGTCATCATCCATCACTATCAAGTTTACAATACATCAAAAATATCA

TTGGTTTGTTGAAGGTCCAGCAACACGTCACACCAAATCTTTAAATTTTTTCAAT

AATTATTAACAGCATTCTTTCACACAAACAAAAAACTCAACAACAACTTCCTCTC

CAACAAGAACAACAAAGATCTATGAAAAAGCCTGAACTCACCGCGACGTCTGTCG

AGAAGTTTCTGATCGAAAAGTTCGACAGCGTCTCCGACCTGATGCAGCTCTCGGA

GGGCGAAGAATCTCGTGCTTTCAGCTTCGATGTAGGAGGGCGTGGATATGTCCTG

CGGGTAAATAGCTGCGCCGATGGTTTCTACAAAGATCGTTATGTTTATCGGCACT

TTGCATCGGCCGCGCTCCCGATTCCGGAAGTGCTTGACATTGGGGAATTCAGCGA

GAGCCTGACCTATTGCATCTCCCGCCGTGCACAGGGTGTCACGTTGCAAGACCTG

CCTGAAACCGAACTGCCCGCTGTTCTGCAGCCGGTCGCGGAGGCCATGGATGCGA

TCGCTGCGGCCGATCTTAGCCAGACGAGCGGGTTCGGCCCATTCGGACCGCAAGG

AATCGGTCAATACACTACATGGCGTGATTTCATATGCGCGATTGCTGATCCCCAT

GTGTATCACTGGCAAACTGTGATGGACGACACCGTCAGTGCGTCCGTCGCGCAGG

CTCTCGATGAGCTGATGCTTTGGGCCGAGGACTGCCCCGAAGTCCGGCACCTCGT

GCACGCGGATTTCGGCTCCAACAATGTCCTGACGGACAATGGCCGCATAACAGCG

GTCATTGACTGGAGCGAGGCGATGTTCGGGGATTCCCAATACGAGGTCGCCAACA

TCTTCTTCTGGAGGCCGTGGTTGGCTTGTATGGAGCAGCAGACGCGCTACTTCGA

GCGGAGGCATCCGGAGCTTGCAGGATCGCCGCGGCTCCGGGCGTATATGCTCCGC

ATTGGTCTTGACCAACTCTATCAGAGCTTGGTTGACGGCAATTTCGATGATGCAG

CTTGGGCGCAGGGTCGATGCGACGCAATCGTCCGATCCGGAGCCGGGACTGTCGG

GCGTACACAAATCGCCCGCAGAAGCGCGGCCGTCTGGACCGATGGCTGTGTAGAA

GTACTCGCCGATAGTGGAAACCGACGCCCCAGCACTCGTCCGAGGGCAAAGGAAT

AGATTGACCTTGGATGCACATTATCAAATTCCATTGTAATAAAACATAAAATCTA

TGTAAAATCATGCATGAGTTGTGTCTTTGTAAAATTGATTTGTAGTCCAAGCCTC

ATTCTTGAAGTTGTCAATTTGAAAGGGAGAAATTGTTGGCATTTACAGTAAGACA

CTTGCTTTCTTTGAGGATGATCAGACATCTCTCAGAAATGCACACCTTTCATCAA

GTGAATGACAATTTCATTGGGAAGGCAACTTTCATTTATGGTTTGGGTCATCATC

CATCACTATCAAGTTTACAATACATCAAAAATATCATTGGTTTGTTGAAGGTCCA

-continued

GCAACACGTCACACCAAATCTTTAAATTTTTTCAATAATTATTAACAGCATTCTT

TCACACAAACAAAAAACTCAACAACAACTTCCTCTCCAACAAGAACAACAAAGCT

TCGAATTCTGCAGTCGACGGTACCGCGGGCCCGGGATCCATCGCCACCATGGTGA

GCAAGGGCGAGGAGCTGTTCACCGGGGTGGTGCCCATCCTGGTCGAGCTGGACGG

CGACGTAAACGGCCACAAGTTCAGCGTGTCCGGCGAGGGCGAGGGCGATGCCACC

TACGGCAAGCTGACCCTGAAGTTCATCTGCACCACCGGCAAGCTGCCCGTGCCCT

GGCCCACCCTCGTGACCACCCTGACCTACGGCGTGCAGTGCTTCAGCCGCTACCC

CGACCACATGAAGCAGCACGACTTCTTCAAGTCCGCCATGCCCGAAGGCTACGTC

CAGGAGCGCACCATCTTCTTCAAGGACGACGGCAACTACAAGACCCGCGCCGAGG

TGAAGTTCGAGGGCGACACCCTGGTGAACCGCATCGAGCTGAAGGGCATCGACTT

CAAGGAGGACGGCAACATCCTGGGGCACAAGCTGGAGTACAACTACAACAGCCAC

AACGTCTATATCATGGCCGACAAGCAGAAGAACGGCATCAAGGTGAACTTCAAGA

TCCGCCACAACATCGAGGACGGCAGCGTGCAGCTCGCCGACCACTACCAGCAGAA

CACCCCCATCGGCGACGGCCCCGTGCTGCTGCCCGACAACCACTACCTGAGCACC

CAGTCCGCCCTGAGCAAAGACCCCAACGAGAAGCGCGATCACATGGTCCTGCTGG

AGTTCGTGACCGCCGCCGGGATCACTCTCGGCATGGACGAGCTGTACAAGTAAAG

CGGCCGCGACTCTAGATCATAATCAGCCATACCACATTTGTAGAGGTTTTACTTG

CTTTAAAAAACCTCCCACACCTCCCCCTGAACCTGAAACATAAAATGAATGCAAT

TGTTGTTGTTAACTTGTTTATTGCAGCTTATAATGGTTACAAATAAAGCAATAGC

ATCACAAATTTCACAAATAAAGCATTTTTTTCACTGCATTCTAGTTGTGGTTTGT

CCAAACTCATCAATGTATCTTAAGGCGTAAATTGTAAGCGTTAATATTTTGTTAA

AATTCGCGTTAAATTTTTGTTAAATCAGCTCATTTTTTAACCAATAGGCCGAAAT

CGGCAAAATCCCTTATAAATCAAAAGAATAGACCGAGATAGGGTTGAGTGTTGTT

CCAGTTTGGAACAAGAGTCCACTATTAAAGAACGTGGACTCCAACGTCAAAGGGC

GAAAAACCGTCTATCAGGGCGATGGCCCACTACGTGAACCATCACCCTAATCAAG

TTTTTTGGGGTCGAGGTGCCGTAAAGCACTAAATCGGAACCCTAAAGGGAGCCCC

CGATTTAGAGCTTGACGGGGAAAGCCGGCGAACGTGGCGAGAAAGGAAGGGAAGA

AAGCGAAAGGAGCGGGCGCTAGGGCGCTGGCAAGTGTAGCGGTCACGCTGCGCGT

AACCACCACACCCGCCGCGCTTAATGCGCCGCTACAGGGCGCGTCAGGTGGCACT

TTTCGGGGAAATGTGCGCGGAACCCCTATTTGTTTATTTTTCTAAATACATTCAA

ATATGTATCCGCTCATGAGACAATAACCCTGATAAATGCTTCAATAATATTGAAA

AAGGAAGAGTCCTGAGGCGGAAAGAACCAGCTGTGGAATGTGTGTCAGTTAGGGT

GTGGAAAGTCCCCAGGCTCCCCAGCAGGCAGAAGTATGCAAAGCATGCATCTCAA

TTAGTCAGCAACCAGGTGTGGAAAGTCCCCAGGCTCCCCAGCAGGCAGAAGTATG

CAAAGCATGCATCTCAATTAGTCAGCAACCATAGTCCCGCCCCTAACTCCGCCCA

TCCCGCCCCTAACTCCGCCCAGTTCCGCCCATTCTCCGCCCCATGGCTGACTAAT

TTTTTTTATTTATGCAGAGGCCGAGGCCGCCTCGGCCTCTGAGCTATTCCAGAAG

TAGTGAGGAGGCTTTTTTGGAGGCCTAGGCTTTTGCAAAGATCGATCAAGAGACA

GGATGAGGATCGTTTCGCATGATTGAACAAGATGGATTGCACGCAGGTTCTCCGG

CCGCTTGGGTGGAGAGGCTATTCGGCTATGACTGGGCACAACAGACAATCGGCTG

-continued
```
CTCTGATGCCGCCGTGTTCCGGCTGTCAGCGCAGGGGCGCCCGGTTCTTTTTGTC

AAGACCGACCTGTCCGGTGCCCTGAATGAACTGCAAGACGAGGCAGCGCGGCTAT

CGTGGCTGGCCACGACGGGCGTTCCTTGCGCAGCTGTGCTCGACGTTGTCACTGA

AGCGGGAAGGGACTGGCTGCTATTGGGCGAAGTGCCGGGGCAGGATCTCCTGTCA

TCTCACCTTGCTCCTGCCGAGAAAGTATCCATCATGGCTGATGCAATGCGGCGGC

TGCATACGCTTGATCCGGCTACCTGCCCATTCGACCACCAAGCGAAACATCGCAT

CGAGCGAGCACGTACTCGGATGGAAGCCGGTCTTGTCGATCAGGATGATCTGGAC

GAAGAGCATCAGGGGCTCGCGCCAGCCGAACTGTTCGCCAGGCTCAAGGCGAGCA

TGCCCGACGGCGAGGATCTCGTCGTGACCCATGGCGATGCCTGCTTGCCGAATAT

CATGGTGGAAAATGGCCGCTTTTCTGGATTCATCGACTGTGGCCGGCTGGGTGTG

GCGGACCGCTATCAGGACATAGCGTTGGCTACCCGTGATATTGCTGAAGAGCTTG

GCGGCGAATGGGCTGACCGCTTCCTCGTGCTTTACGGTATCGCCGCTCCCGATTC

GCAGCGCATCGCCTTCTATCGCCTTCTTGACGAGTTCTTCTGAGCGGGACTCTGG

GGTTCGAAATGACCGACCAAGCGACGCCCAACCTGCCATCACGAGATTTCGATTC

CACCGCCGCCTTCTATGAAAGGTTGGGCTTCGGAATCGTTTTCCGGGACGCCGGC

TGGATGATCCTCCAGCGCGGGGATCTCATGCTGGAGTTCTTCGCCCACCCTAGGG

GGAGGCTAACTGAAACACGGAAGGAGACAATACCGGAAGGAACCCGCGCTATGAC

GGCAATAAAAAGACAGAATAAAACGCACGGTGTTGGGTCGTTTGTTCATAAACGC

GGGGTTCGGTCCCAGGGCTGGCACTCTGTCGATACCCCACCGAGACCCCATTGGG

GCCAATACGCCCGCGTTTCTTCCTTTTCCCCACCCCACCCCCCAAGTTCGGGTGA

AGGCCCAGGGCTCGCAGCCAACGTCGGGGCGGCAGGCCCTGCCATAGCCTCAGGT

TACTCATATATACTTTAGATTGATTTAAAACTTCATTTTTAATTTAAAAGGATCT

AGGTGAAGATCCTTTTTGATAATCTCATGACCAAAATCCCTTAACGTGAGTTTTC

GTTCCACTGAGCGTCAGACCCCGTAGAAAAGATCAAAGGATCTTCTTGAGATCCT

TTTTTTCTGCGCGTAATCTGCTGCTTGCAAACAAAAAAACCACCGCTACCAGCGG

TGGTTTGTTTGCCGGATCAAGAGCTACCAACTCTTTTTCCGAAGGTAACTGGCTT

CAGCAGAGCGCAGATACCAAATACTGTCCTTCTAGTGTAGCCGTAGTTAGGCCAC

CACTTCAAGAACTCTGTAGCACCGCCTACATACCTCGCTCTGCTAATCCTGTTAC

CAGTGGCTGCTGCCAGTGGCGATAAGTCGTGTCTTACCGGGTTGGACTCAAGACG

ATAGTTACCGGATAAGGCGCAGCGGTCGGGCTGAACGGGGGGTTCGTGCACACAG

CCCAGCTTGGAGCGAACGACCTACACCGAACTGAGATACCTACAGCGTGAGCTAT

GAGAAAGCGCCACGCTTCCCGAAGGGAGAAAGGCGGACAGGTATCCGGTAAGCGG

CAGGGTCGGAACAGGAGAGCGCACGAGGGAGCTTCCAGGGGGAAACGCCTGGTAT

CTTTATAGTCCTGTCGGGTTTCGCCACCTCTGACTTGAGCGTCGATTTTTGTGAT

GCTCGTCAGGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCT

GATTCTGTGGATAACCGTATTACCGCCATGCAT
```

EGFP (241 amino acids)
SEQ ID NO: 8
msrvskgeel ftgvvpilve ldgdvnghkf svsgegegda tygkltlkfi cttgklpvpw ptlvttltyg vqcfsrypdh mkqhdffksa mpegyvqert iffkddgnyk traevkfegd tlvnrielkg idfkedgnil ghkleynyns -continued hnvyimadkq kngikvnfki rhniedgsvq ladhyqqntp igdgpvllpd nhylstqsal skdpnekrdh mvllefvtaa gitlgmdely k EGFP (1150 nt)

SEQ ID NO: 9

ATGTCTAGAG TGAGCAAGGG CGAGGAGCTG TTCACCGGGG TGGTGCCCAT

CCTGGTCGAG CTGGACGGCG ACGTAAACGG CCACAAGTTC AGCGTGTCCG

GCGAGGGCGA GGGCGATGCC ACCTACGGCA AGCTGACCCT GAAGTTCATC

TGCACCACCG GCAAGCTGCC CGTGCCCTGG CCCACCCTCG TGACCACCCT

GACCTACGGC GTGCAGTGCT TCAGCCGCTA CCCCGACCAC ATGAAGCAGC

ACGACTTCTT CAAGTCCGCC ATGCCCGAAG GCTACGTCCA GGAGGTAGAT

TTATGCATCC TCTTGTCATG AGAAGTCGAA TTGTTCCCAT TCTGTGTGTT

GCAGCTACAG ATGGAGATAC ATAGAGATAC TCGTGGATTT TGCTTAGTGT

TGAGTTTTGT TCTGGTTGTG AACTAAAAGT TTATACATTT GCAGGAAATA

AATAGCCTTT TGTTTAAATC AAAAGGTCTT ACCTATGTTA GTGTGAAGCA

TTGGATCCCA AAGAACTCCA AAATGCGATG AGGCATATTT AATCTTGTCT

GGACTAGTAA CAGGTTGGGA TGACCACCTG TGAAGCTCCA ACAGGATTGC

CTCCTCACGC AATGTTTGAG GTCTGATGTT CAATAGCTTG TTTTGTTTCA

CTTTGCTTTG GACTTTCTTT TCGCCAATGA GCTATGTTTC TGATGGTTTT

CACTCTTTTG GTGTGTAGAG AACCATCTTC TTCAAGGACG ACGGCAACTA

CAAGACCCGC GCCGAGGTGA AGTTCGAGGG CGACACCCTG GTGAACCGCA

TCGAGCTGAA GGGCATCGAC TTCAAGGAGG ACGGCAACAT CCTGGGGCAC

AAGCTGGAGT ACAACTACAA CAGCCACAAC GTCTATATCA TGGCCGACAA

GCAGAAGAAC GGCATCAAGG TGAACTTCAA GATCCGCCAC AACATCGAGG

ACGGCAGCGT GCAGCTCGCC GACCACTACC AGCAGAACAC CCCCATCGGC

GACGGCCCCG TGCTGCTGCC CGACAACCAC TACCTGAGCA CCCAGTCCGC

CCTGAGCAAA GACCCCAACG AGAAGCGCGA TCACATGGTC CTGCTGGAGT

TCGTGACCGC CGCCGGGATC ACTCTCGGCA TGGACGAGCT GTACAAGTAA

GT-rich domain (30 nt)

SEQ ID NO: 10

GTTGTGTCTTTGTAAAATTGATTTGTAGTC

The invention claimed is:

1. An expression vector comprising:

a promoter comprising the polynucleotide sequence of SEQ ID NO: 4;

a selection marker comprising the hygromycin resistance gene; and a nucleic acid encoding a polypeptide of interest, operably linked to the promoter, wherein the vector comprises the polynucleotide sequence of SEQ ID NO: 7.

2. The vector of claim 1, wherein the vector does not include a cytomegalovirus (CMV) promoter.

3. The vector of claim 1, wherein the vector further comprises a polynucleotide encoding a fluorescent protein.

4. The vector of claim 3, wherein the polynucleotide encoding a fluorescent protein is operably linked to the promoter and to the polynucleotide encoding the polypeptide of interest.

5. An amoeba transformed with the vector of claim 1.

6. The amoeba of claim 5, wherein the amoeba has reduced virulence compared to the corresponding amoeba lacking the vector.

7. The amoeba of claim 6, wherein the corresponding amoeba is an untransformed amoeba or an amoeba transformed with a different vector.

8. A vaccine comprising the amoeba of claim 5.

9. A method of expressing a foreign protein in an amoeba, the method comprising:

transforming an amoeba with the vector of claim 1, wherein the polypeptide of interest comprises the foreign protein;

isolating the transformed amoeba;

culturing the transformed amoeba; and expressing the foreign protein in the amoeba.

10. A method of manipulating an amoeba, the method comprising transforming the amoeba with the vector of claim 1.

11. The method of claim 9, wherein the transforming is performed by electroporation.

12. The method of claim 9, wherein the amoeba is cultured in the presence of hygromycin, puromycin, nourseothricin, bleomycin, or a combination thereof.

* * * * *

SEQUENCE LISTING

<160> NUMBER OF SEQ ID NOS: 10

<210> SEQ ID NO 1
<211> LENGTH: 4729
<212> TYPE: DNA
<213> ORGANISM: Artificial Sequence
<220> FEATURE:
<223> OTHER INFORMATION: Synthetic

<400> SEQUENCE: 1
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240

```
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccatcgc caccatggtg agcaagggcg aggagctgtt caccggggtg gtgcccatcc    720
tggtcgagct ggacggcgac gtaaacggcc acaagttcag cgtgtccggc gagggcgagg    780
gcgatgccac ctacggcaag ctgaccctga agttcatctg caccaccggc aagctgcccg    840
tgccctggcc caccctcgtg accaccctga cctacggcgt gcagtgcttc agccgctacc    900
ccgaccacat gaagcagcac gacttcttca agtccgccat gcccgaaggc tacgtccagg    960
agcgcaccat cttcttcaag gacgacggca actacaagac ccgcgccgag gtgaagttcg   1020
agggcgacac cctggtgaac cgcatcgagc tgaagggcat cgacttcaag gaggacggca   1080
acatcctggg gcacaagctg gagtacaact acaacagcca caacgtctat atcatggccg   1140
acaagcagaa gaacggcatc aaggtgaact tcaagatccg ccacaacatc gaggacggca   1200
gcgtgcagct cgccgaccac taccagcaga acacccccat cggcgacggc cccgtgctgc   1260
tgcccgacaa ccactacctg agcacccagt ccgccctgag caaagacccc aacgagaagc   1320
gcgatcacat ggtcctgctg gagttcgtga ccgccgccgg gatcactctc ggcatggacg   1380
agctgtacaa gtaaagcggc cgcgactcta gatcataatc agccatacca catttgtaga   1440
ggttttactt gctttaaaaa acctcccaca cctccccctg aacctgaaac ataaaatgaa   1500
tgcaattgtt gttgttaact tgtttattgc agcttataat ggttacaaat aaagcaatag   1560
catcacaaat ttcacaaata aagcattttt ttcactgcat tctagttgtg gtttgtccaa   1620
actcatcaat gtatcttaag gcgtaaattg taagcgttaa tattttgtta aaattcgcgt   1680
taaatttttg ttaaatcagc tcatttttta accaataggc cgaaatcggc aaaatccctt   1740
ataaatcaaa agaatagacc gagatagggt tgagtgttgt tccagtttgg aacaagagtc   1800
cactattaaa gaacgtggac tccaacgtca aagggcgaaa aaccgtctat cagggcgatg   1860
gcccactacg tgaaccatca ccctaatcaa gtttttttggg gtcgaggtgc cgtaaagcac  1920
taaatcggaa ccctaaaggg agcccccgat ttagagcttg acggggaaag ccggcgaacg   1980
tggcgagaaa ggaagggaag aaagcgaaag gagcgggcgc tagggcgctg gcaagtgtag   2040
cggtcacgct gcgcgtaacc accacacccg ccgcgcttaa tgcgccgcta cagggcgcgt   2100
caggtggcac ttttcgggga aatgtgcgcg gaacccctat ttgtttattt ttctaaatac   2160
attcaaatat gtatccgctc atgagacaat aaccctgata aatgcttcaa taatattgaa   2220
aaaggaagag tcctgaggcg gaaagaacca gctgtggaat gtgtgtcagt tagggtgtgg   2280
aaagtcccca ggctccccag caggcagaag tatgcaaagc atgcatctca attagtcagc   2340
aaccaggtgt ggaaagtccc caggctcccc agcaggcaga agtatgcaaa gcatgcatct   2400
caattagtca gcaaccatag tcccgcccct aactccgccc atcccgcccc taactccgcc   2460
cagttccgcc cattctccgc cccatggctg actaattttt tttatttatg cagaggccga   2520
ggccgcctcg gcctctgagc tattccagaa gtagtgagga ggcttttttg gaggcctagg   2580
```

-continued

```
cttttgcaaa gatcgatcaa gagacaggat gaggatcgtt tcgcatgatt gaacaagatg   2640

gattgcacgc aggttctccg gccgcttggg tggagaggct attcggctat gactgggcac   2700

aacagacaat cggctgctct gatgccgccg tgttccggct gtcagcgcag gggcgcccgg   2760

ttctttttgt caagaccgac ctgtccggtg ccctgaatga actgcaagac gaggcagcgc   2820

ggctatcgtg gctggccacg acgggcgttc cttgcgcagc tgtgctcgac gttgtcactg   2880

aagcgggaag ggactggctg ctattgggcg aagtgccggg gcaggatctc ctgtcatctc   2940

accttgctcc tgccgagaaa gtatccatca tggctgatgc aatgcggcgg ctgcatacgc   3000

ttgatccggc tacctgccca ttcgaccacc aagcgaaaca tcgcatcgag cgagcacgta   3060

ctcggatgga agccggtctt gtcgatcagg atgatctgga cgaagagcat caggggctcg   3120

cgccagccga actgttcgcc aggctcaagg cgagcatgcc cgacggcgag gatctcgtcg   3180

tgacccatgg cgatgcctgc ttgccgaata tcatggtgga aaatggccgc ttttctggat   3240

tcatcgactg tggccggctg ggtgtggcgg accgctatca ggacatagcg ttggctaccc   3300

gtgatattgc tgaagagctt ggcggcgaat gggctgaccg cttcctcgtg ctttacggta   3360

tcgccgctcc cgattcgcag cgcatcgcct tctatcgcct tcttgacgag ttcttctgag   3420

cgggactctg gggttcgaaa tgaccgacca agcgacgccc aacctgccat cacgagattt   3480

cgattccacc gccgccttct atgaaaggtt gggcttcgga atcgttttcc gggacgccgg   3540

ctggatgatc ctccagcgcg gggatctcat gctggagttc ttcgcccacc ctagggggag   3600

gctaactgaa acacggaagg agacaatacc ggaaggaacc cgcgctatga cggcaataaa   3660

aagacagaat aaaacgcacg gtgttgggtc gtttgttcat aaacgcgggg ttcggtccca   3720

gggctggcac tctgtcgata ccccaccgag accccattgg ggccaatacg cccgcgtttc   3780

ttccttttcc ccaccccacc ccccaagttc gggtgaaggc ccagggctcg cagccaacgt   3840

cggggcggca ggccctgcca tagcctcagg ttactcatat atactttaga ttgatttaaa   3900

acttcatttt taatttaaaa ggatctaggt gaagatcctt tttgataatc tcatgaccaa   3960

aatcccttaa cgtgagtttt cgttccactg agcgtcagac cccgtagaaa agatcaaagg   4020

atcttcttga gatccttttt ttctgcgcgt aatctgctgc ttgcaaacaa aaaaaccacc   4080

gctaccagcg gtggtttgtt tgccggatca agagctacca actctttttc cgaaggtaac   4140

tggcttcagc agagcgcaga taccaaatac tgtccttcta gtgtagccgt agttaggcca   4200

ccacttcaag aactctgtag caccgcctac atacctcgct ctgctaatcc tgttaccagt   4260

ggctgctgcc agtggcgata agtcgtgtct taccgggttg gactcaagac gatagttacc   4320

ggataaggcg cagcggtcgg gctgaacggg gggttcgtgc acacagccca gcttggagcg   4380

aacgacctac accgaactga gatacctaca gcgtgagcta tgagaaagcg ccacgcttcc   4440

cgaagggaga aaggcggaca ggtatccggt aagcggcagg gtcggaacag gagagcgcac   4500

gagggagctt ccagggggaa acgcctggta tctttatagt cctgtcgggt ttcgccacct   4560

ctgacttgag cgtcgatttt tgtgatgctc gtcagggggg cggagcctat ggaaaaacgc   4620

cagcaacgcg gcctttttac ggttcctggc cttttgctgg ccttttgctc acatgttctt   4680

tcctgcgtta tcccctgatt ctgtggataa ccgtattacc gccatgcat              4729
```

<210> SEQ ID NO 2
<211> LENGTH: 75
<212> TYPE: DNA
<213> ORGANISM: Artificial Sequence
<220> FEATURE:
<223> OTHER INFORMATION: Synthetic -continued

<400> SEQUENCE: 2
gctagcgcta ccggactcag atctcgagct caagcttcga attctgcagt cgacggtacc 60
gcgggcccgg gatcc 75

<210> SEQ ID NO 3
<211> LENGTH: 44
<212> TYPE: DNA
<213> ORGANISM: Artificial Sequence
<220> FEATURE:
<223> OTHER INFORMATION: Synthetic

<400> SEQUENCE: 3
aagcttcgaa ttctgcagtc gacggtaccg cgggcccggg atcc 44

<210> SEQ ID NO 4
<211> LENGTH: 335
<212> TYPE: DNA
<213> ORGANISM: Artificial Sequence
<220> FEATURE:
<223> OTHER INFORMATION: Synthetic

<400> SEQUENCE: 4
caagcctcat tcttgaagtt gtcaatttga aagggagaaa ttgttggcat ttacagtaag 60
acacttgctt tctttgagga tgatcagaca tctctcagaa atgcacacct ttcatcaagt 120
gaatgacaat ttcattggga aggcaacttt catttatggt ttgggtcatc atccatcact 180
atcaagttta caatacatca aaaatatcat tggtttgttg aaggtccagc aacacgtcac 240
accaaatctt taaatttttt caataattat taacagcatt ctttcacaca aacaaaaaac 300
tcaacaacaa cttcctctcc aacaagaaca acaaa 335

<210> SEQ ID NO 5
<211> LENGTH: 100
<212> TYPE: DNA
<213> ORGANISM: Artificial Sequence
<220> FEATURE:
<223> OTHER INFORMATION: Synthetic

<400> SEQUENCE: 5
attgaccttg gatgcacatt atcaaattcc attgtaataa aacataaaat ctatgtaaaa 60
tcatgcatga gttgtgtctt tgtaaaattg atttgtagtc 100

<210> SEQ ID NO 6
<211> LENGTH: 1026
<212> TYPE: DNA
<213> ORGANISM: Artificial Sequence
<220> FEATURE:
<223> OTHER INFORMATION: Synthetic

<400> SEQUENCE: 6
atgaaaaagc ctgaactcac cgcgacgtct gtcgagaagt ttctgatcga aaagttcgac 60
agcgtctccg acctgatgca gctctcggag ggcgaagaat ctcgtgcttt cagcttcgat 120
gtaggagggc gtggatatgt cctgcgggta aatagctgcg ccgatggttt ctacaaagat 180
cgttatgttt atcggcactt tgcatcggcc gcgctcccga ttccggaagt gcttgacatt 240
ggggaattca gcgagagcct gacctattgc atctcccgcc gtgcacaggg tgtcacgttg 300
caagacctgc ctgaaaccga actgcccgct gttctgcagc cggtcgcgga ggccatggat 360
gcgatcgctg cggccgatct tagccagacg agcgggttcg gcccattcgg accgcaagga 420

-continued

```
atcggtcaat acactacatg gcgtgatttc atatgcgcga ttgctgatcc ccatgtgtat    480

cactggcaaa ctgtgatgga cgacaccgtc agtgcgtccg tcgcgcaggc tctcgatgag    540

ctgatgcttt gggccgagga ctgccccgaa gtccggcacc tcgtgcacgc ggatttcggc    600

tccaacaatg tcctgacgga caatggccgc ataacagcgg tcattgactg gagcgaggcg    660

atgttcgggg attcccaata cgaggtcgcc aacatcttct tctggaggcc gtggttggct    720

tgtatggagc agcagacgcg ctacttcgag cggaggcatc cggagcttgc aggatcgccg    780

cggctccggg cgtatatgct ccgcattggt cttgaccaac tctatcagag cttggttgac    840

ggcaatttcg atgatgcagc ttgggcgcag ggtcgatgcg acgcaatcgt ccgatccgga    900

gccgggactg tcgggcgtac acaaatcgcc cgcagaagcg cggccgtctg gaccgatggc    960

tgtgtagaag tactcgccga tagtggaaac cgacgcccca gcactcgtcc gagggcaaag   1020

gaatag                                                             1026
```

<210> SEQ ID NO 7
<211> LENGTH: 5918
<212> TYPE: DNA
<213> ORGANISM: Artificial Sequence
<220> FEATURE:
<223> OTHER INFORMATION: Synthetic

<400> SEQUENCE: 7

```
tagttattat gcaagcctca ttcttgaagt tgtcaatttg aaagggagaa attgttggca     60

tttacagtaa gacacttgct ttctttgagg atgatcagac atctctcaga aatgcacacc    120

tttcatcaag tgaatgacaa tttcattggg aaggcaactt tcatttatgg tttgggtcat    180

catccatcac tatcaagttt acaatacatc aaaaatatca ttggtttgtt gaaggtccag    240

caacacgtca caccaaatct ttaaattttt tcaataatta ttaacagcat tctttcacac    300

aaacaaaaaa ctcaacaaca acttcctctc caacaagaac aacaaagatc tatgaaaaag    360

cctgaactca ccgcgacgtc tgtcgagaag tttctgatcg aaaagttcga cagcgtctcc    420

gacctgatgc agctctcgga gggcgaagaa tctcgtgctt tcagcttcga tgtaggaggg    480

cgtggatatg tcctgcgggt aaatagctgc gccgatggtt tctacaaaga tcgttatgtt    540

tatcggcact ttgcatcggc cgcgctcccg attccggaag tgcttgacat tggggaattc    600

agcgagagcc tgacctattg catctcccgc cgtgcacagg gtgtcacgtt gcaagacctg    660

cctgaaaccg aactgcccgc tgttctgcag ccggtcgcgg aggccatgga tgcgatcgct    720

gcggccgatc ttagccagac gagcgggttc ggcccattcg gaccgcaagg aatcggtcaa    780

tacactacat ggcgtgattt catatgcgcg attgctgatc cccatgtgta tcactggcaa    840

actgtgatgg acgacaccgt cagtgcgtcc gtcgcgcagg ctctcgatga gctgatgctt    900

tgggccgagg actgccccga agtccggcac ctcgtgcacg cggatttcgg ctccaacaat    960

gtcctgacgg acaatggccg cataacagcg gtcattgact ggagcgaggc gatgttcggg   1020

gattcccaat acgaggtcgc caacatcttc ttctggaggc cgtggttggc ttgtatggag   1080

cagcagacgc gctacttcga gcggaggcat ccggagcttg caggatcgcc gcggctccgg   1140

gcgtatatgc tccgcattgg tcttgaccaa ctctatcaga gcttggttga cggcaatttc   1200

gatgatgcag cttgggcgca gggtcgatgc gacgcaatcg tccgatccgg agccgggact   1260

gtcgggcgta cacaaatcgc ccgcagaagc gcggccgtct ggaccgatgg ctgtgtagaa   1320

gtactcgccg atagtggaaa ccgacgcccc agcactcgtc cgagggcaaa ggaatagatt   1380

gaccttggat gcacattatc aaattccatt gtaataaaac ataaaatcta tgtaaaatca   1440
```

-continued

```
tgcatgagtt gtgtctttgt aaaattgatt tgtagtccaa gcctcattct tgaagttgtc   1500
aatttgaaag ggagaaattg ttggcattta cagtaagaca cttgctttct ttgaggatga   1560
tcagacatct ctcagaaatg cacacctttc atcaagtgaa tgacaatttc attgggaagg   1620
caactttcat ttatggtttg ggtcatcatc catcactatc aagtttacaa tacatcaaaa   1680
atatcattgg tttgttgaag gtccagcaac acgtcacacc aaatctttaa attttttcaa   1740
taattattaa cagcattctt tcacacaaac aaaaaactca acaacaactt cctctccaac   1800
aagaacaaca aagcttcgaa ttctgcagtc gacggtaccg cgggcccggg atccatcgcc   1860
accatggtga gcaagggcga ggagctgttc accggggtgg tgcccatcct ggtcgagctg   1920
gacggcgacg taaacggcca caagttcagc gtgtccggcg agggcgaggg cgatgccacc   1980
tacggcaagc tgaccctgaa gttcatctgc accaccggca agctgcccgt gccctggccc   2040
accctcgtga ccaccctgac ctacggcgtg cagtgcttca gccgctaccc cgaccacatg   2100
aagcagcacg acttcttcaa gtccgccatg cccgaaggct acgtccagga gcgcaccatc   2160
ttcttcaagg acgacggcaa ctacaagacc cgcgccgagg tgaagttcga gggcgacacc   2220
ctggtgaacc gcatcgagct gaagggcatc gacttcaagg aggacggcaa catcctgggg   2280
cacaagctgg agtacaacta caacagccac aacgtctata tcatggccga caagcagaag   2340
aacggcatca aggtgaactt caagatccgc cacaacatcg aggacggcag cgtgcagctc   2400
gccgaccact accagcagaa cacccccatc ggcgacggcc ccgtgctgct gcccgacaac   2460
cactacctga gcacccagtc cgccctgagc aaagacccca acgagaagcg cgatcacatg   2520
gtcctgctgg agttcgtgac cgccgccggg atcactctcg gcatggacga gctgtacaag   2580
taaagcggcc gcgactctag atcataatca gccataccac atttgtagag gttttacttg   2640
ctttaaaaaa cctcccacac ctccccctga acctgaaaca taaaatgaat gcaattgttg   2700
ttgttaactt gtttattgca gcttataatg gttacaaata aagcaatagc atcacaaatt   2760
tcacaaataa agcatttttt tcactgcatt ctagttgtgg tttgtccaaa ctcatcaatg   2820
tatcttaagg cgtaaattgt aagcgttaat attttgttaa aattcgcgtt aaatttttgt   2880
taaatcagct cattttttaa ccaataggcc gaaatcggca aaatccctta taaatcaaaa   2940
gaatagaccg agatagggtt gagtgttgtt ccagtttgga acaagagtcc actattaaag   3000
aacgtggact ccaacgtcaa agggcgaaaa accgtctatc agggcgatgg cccactacgt   3060
gaaccatcac cctaatcaag ttttttgggg tcgaggtgcc gtaaagcact aaatcggaac   3120
cctaaaggga gcccccgatt tagagcttga cggggaaagc cggcgaacgt ggcgagaaag   3180
gaagggaaga aagcgaaagg agcgggcgct agggcgctgg caagtgtagc ggtcacgctg   3240
cgcgtaacca ccacacccgc cgcgcttaat gcgccgctac agggcgcgtc aggtggcact   3300
tttcggggaa atgtgcgcgg aacccctatt tgtttatttt tctaaataca ttcaaatatg   3360
tatccgctca tgagacaata accctgataa atgcttcaat aatattgaaa aaggaagagt   3420
cctgaggcgg aaagaaccag ctgtggaatg tgtgtcagtt agggtgtgga aagtccccag   3480
gctccccagc aggcagaagt atgcaaagca tgcatctcaa ttagtcagca accaggtgtg   3540
gaaagtcccc aggctcccca gcaggcagaa gtatgcaaag catgcatctc aattagtcag   3600
caaccatagt cccgccccta actccgccca tcccgcccct aactccgccc agttccgccc   3660
attctccgcc ccatggctga ctaatttttt ttatttatgc agaggccgag gccgcctcgg   3720
cctctgagct attccagaag tagtgaggag gcttttttgg aggcctaggc ttttgcaaag   3780
```

-continued

```
atcgatcaag agacaggatg aggatcgttt cgcatgattg aacaagatgg attgcacgca   3840

ggttctccgg ccgcttgggt ggagaggcta ttcggctatg actgggcaca acagacaatc   3900

ggctgctctg atgccgccgt gttccggctg tcagcgcagg ggcgcccggt tctttttgtc   3960

aagaccgacc tgtccggtgc cctgaatgaa ctgcaagacg aggcagcgcg gctatcgtgg   4020

ctggccacga cgggcgttcc ttgcgcagct gtgctcgacg ttgtcactga agcgggaagg   4080

gactggctgc tattgggcga agtgccgggg caggatctcc tgtcatctca ccttgctcct   4140

gccgagaaag tatccatcat ggctgatgca atgcggcggc tgcatacgct tgatccggct   4200

acctgcccat tcgaccacca agcgaaacat cgcatcgagc gagcacgtac tcggatggaa   4260

gccggtcttg tcgatcagga tgatctggac gaagagcatc aggggctcgc gccagccgaa   4320

ctgttcgcca ggctcaaggc gagcatgccc gacggcgagg atctcgtcgt gacccatggc   4380

gatgcctgct tgccgaatat catggtggaa aatggccgct tttctggatt catcgactgt   4440

ggccggctgg gtgtggcgga ccgctatcag gacatagcgt tggctacccg tgatattgct   4500

gaagagcttg gcggcgaatg ggctgaccgc ttcctcgtgc tttacggtat cgccgctccc   4560

gattcgcagc gcatcgcctt ctatcgcctt cttgacgagt tcttctgagc gggactctgg   4620

ggttcgaaat gaccgaccaa gcgacgccca acctgccatc acgagatttc gattccaccg   4680

ccgccttcta tgaaaggttg ggcttcggaa tcgttttccg ggacgccggc tggatgatcc   4740

tccagcgcgg ggatctcatg ctggagttct tcgcccaccc tagggggagg ctaactgaaa   4800

cacggaagga gacaataccg gaaggaaccc gcgctatgac ggcaataaaa agacagaata   4860

aaacgcacgg tgttgggtcg tttgttcata aacgcggggt tcggtcccag ggctggcact   4920

ctgtcgatac cccaccgaga ccccattggg gccaatacgc ccgcgtttct tccttttccc   4980

caccccaccc cccaagttcg ggtgaaggcc cagggctcgc agccaacgtc ggggcggcag   5040

gccctgccat agcctcaggt tactcatata tactttagat tgatttaaaa cttcattttt   5100

aatttaaaag gatctaggtg aagatccttt ttgataatct catgaccaaa atcccttaac   5160

gtgagttttc gttccactga gcgtcagacc ccgtagaaaa gatcaaagga tcttcttgag   5220

atcctttttt tctgcgcgta atctgctgct tgcaaacaaa aaaaccaccg ctaccagcgg   5280

tggtttgttt gccggatcaa gagctaccaa ctctttttcc gaaggtaact ggcttcagca   5340

gagcgcagat accaaatact gtccttctag tgtagccgta gttaggccac cacttcaaga   5400

actctgtagc accgcctaca tacctcgctc tgctaatcct gttaccagtg gctgctgcca   5460

gtggcgataa gtcgtgtctt accgggttgg actcaagacg atagttaccg gataaggcgc   5520

agcggtcggg ctgaacgggg ggttcgtgca cacagcccag cttggagcga acgacctaca   5580

ccgaactgag atacctacag cgtgagctat gagaaagcgc cacgcttccc gaagggagaa   5640

aggcggacag gtatccggta agcggcaggg tcggaacagg agagcgcacg agggagcttc   5700

caggggggaaa cgcctggtat ctttatagtc ctgtcgggtt tcgccacctc tgacttgagc   5760

gtcgattttt gtgatgctcg tcaggggggc ggagcctatg gaaaaacgcc agcaacgcgg   5820

cctttttacg gttcctggcc ttttgctggc cttttgctca catgttcttt cctgcgttat   5880

cccctgattc tgtggataac cgtattaccg ccatgcat                           5918
```

<210> SEQ ID NO 8
<211> LENGTH: 241
<212> TYPE: PRT
<213> ORGANISM: Artificial Sequence
<220> FEATURE:
<223> OTHER INFORMATION: Synthetic

<400> SEQUENCE: 8

Met Ser Arg Val Ser Lys Gly Glu Glu Leu Phe Thr Gly Val Val Pro
1 5 10 15

Ile Leu Val Glu Leu Asp Gly Asp Val Asn Gly His Lys Phe Ser Val
20 25 30

Ser Gly Glu Gly Glu Gly Asp Ala Thr Tyr Gly Lys Leu Thr Leu Lys
35 40 45

Phe Ile Cys Thr Thr Gly Lys Leu Pro Val Pro Trp Pro Thr Leu Val
50 55 60

Thr Thr Leu Thr Tyr Gly Val Gln Cys Phe Ser Arg Tyr Pro Asp His
65 70 75 80

Met Lys Gln His Asp Phe Phe Lys Ser Ala Met Pro Glu Gly Tyr Val
85 90 95

Gln Glu Arg Thr Ile Phe Phe Lys Asp Asp Gly Asn Tyr Lys Thr Arg
100 105 110

Ala Glu Val Lys Phe Glu Gly Asp Thr Leu Val Asn Arg Ile Glu Leu
115 120 125

Lys Gly Ile Asp Phe Lys Glu Asp Gly Asn Ile Leu Gly His Lys Leu
130 135 140

Glu Tyr Asn Tyr Asn Ser His Asn Val Tyr Ile Met Ala Asp Lys Gln
145 150 155 160

Lys Asn Gly Ile Lys Val Asn Phe Lys Ile Arg His Asn Ile Glu Asp
165 170 175

Gly Ser Val Gln Leu Ala Asp His Tyr Gln Gln Asn Thr Pro Ile Gly
180 185 190

Asp Gly Pro Val Leu Leu Pro Asp Asn His Tyr Leu Ser Thr Gln Ser
195 200 205

Ala Leu Ser Lys Asp Pro Asn Glu Lys Arg Asp His Met Val Leu Leu
210 215 220

Glu Phe Val Thr Ala Ala Gly Ile Thr Leu Gly Met Asp Glu Leu Tyr
225 230 235 240

Lys

<210> SEQ ID NO 9
<211> LENGTH: 1150
<212> TYPE: DNA
<213> ORGANISM: Artificial Sequence
<220> FEATURE:
<223> OTHER INFORMATION: Synthetic

<400> SEQUENCE: 9
atgtctagag tgagcaaggg cgaggagctg ttcaccgggg tggtgcccat cctggtcgag 60
ctggacggcg acgtaaacgg ccacaagttc agcgtgtccg gcgagggcga gggcgatgcc 120
acctacggca agctgaccct gaagttcatc tgcaccaccg gcaagctgcc cgtgccctgg 180
cccaccctcg tgaccaccct gacctacggc gtgcagtgct tcagccgcta ccccgaccac 240
atgaagcagc acgacttctt caagtccgcc atgcccgaag gctacgtcca ggaggtagat 300
ttatgcatcc tcttgtcatg agaagtcgaa ttgttcccat tctgtgtgtt gcagctacag 360
atggagatac atagagatac tcgtggattt tgcttagtgt tgagttttgt tctggttgtg 420
aactaaaagt ttatacattt gcaggaaata aatagccttt tgtttaaatc aaaaggtctt 480
acctatgtta gtgtgaagca ttggatccca aagaactcca aaatgcgatg aggcatattt 540
aatcttgtct ggactagtaa caggttggga tgaccacctg tgaagctcca acaggattgc 600

-continued

```
ctcctcacgc aatgtttgag gtctgatgtt caatagcttg ttttgtttca ctttgctttg    660

gactttcttt tcgccaatga gctatgtttc tgatggtttt cactcttttg gtgtgtagag    720

aaccatcttc ttcaaggacg acggcaacta caagacccgc gccgaggtga agttcgaggg    780

cgacaccctg gtgaaccgca tcgagctgaa gggcatcgac ttcaaggagg acggcaacat    840

cctggggcac aagctggagt acaactacaa cagccacaac gtctatatca tggccgacaa    900

gcagaagaac ggcatcaagg tgaacttcaa gatccgccac aacatcgagg acggcagcgt    960

gcagctcgcc gaccactacc agcagaacac ccccatcggc gacggccccg tgctgctgcc   1020

cgacaaccac tacctgagca cccagtccgc cctgagcaaa gaccccaacg agaagcgcga   1080

tcacatggtc ctgctggagt tcgtgaccgc cgccgggatc actctcggca tggacgagct   1140

gtacaagtaa                                                           1150


<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10

gttgtgtctt tgtaaaattg atttgtagtc                                       30
```